US010206698B2

(12) United States Patent
Hakala et al.

(10) Patent No.: US 10,206,698 B2
(45) Date of Patent: *Feb. 19, 2019

(54) LOW PROFILE ELECTRODES FOR AN ANGIOPLASTY SHOCK WAVE CATHETER

(71) Applicant: SHOCKWAVE MEDICAL, INC., Fremont, CA (US)

(72) Inventors: Doug Hakala, Woodinville, WA (US); John M. Adams, Snohomish, WA (US); Khoi T. Le, San Jose, CA (US); Show-Mean Steve Wu, Fremont, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 378 days.

This patent is subject to a terminal disclaimer.

(21) Appl. No.: 15/220,999

(22) Filed: Jul. 27, 2016

(65) Prior Publication Data

US 2016/0331389 A1    Nov. 17, 2016

Related U.S. Application Data

(63) Continuation of application No. 14/515,130, filed on Oct. 15, 2014, now Pat. No. 9,433,428, which is a
(Continued)

(51) Int. Cl.
*A61B 17/22* (2006.01)

(52) U.S. Cl.
CPC .... *A61B 17/2202* (2013.01); *A61B 17/22022* (2013.01); *A61B 2017/22001* (2013.01);
(Continued)

(58) Field of Classification Search
CPC .... A61B 17/22222; A61B 2017/22001; A61B 2017/22022; A61B 2017/22028; A61B 2017/22062; A61B 2017/22025

See application file for complete search history.

(56) References Cited

U.S. PATENT DOCUMENTS 3,413,976 A    12/1968 Roze
3,785,382 A    1/1974 Schmidt et al.
(Continued)

FOREIGN PATENT DOCUMENTS

CN    1269708 A    10/2000
CN    102057422 A    5/2011
(Continued)

OTHER PUBLICATIONS

Decision to Grant received for European Patent Application No. 13756766.5, dated May 27, 2016, 2 pages.
(Continued)

*Primary Examiner* — Sarah W Aleman
*Assistant Examiner* — Rachel S Highland
(74) *Attorney, Agent, or Firm* — Morrison & Foerster LLP

(57) ABSTRACT

Described herein are low-profile electrodes for use with an angioplasty shockwave catheter. A low-profile electrode assembly may have an inner electrode, an insulating layer disposed over the inner electrode such that an opening in the insulating layer is aligned with the inner electrode, and an outer electrode sheath disposed over the insulating layer such that an opening in the outer electrode sheath is coaxially aligned with the opening in the insulating layer. This layered configuration allows for the generation of shockwaves that propagate outward from the side of the catheter. In some variations, the electrode assembly has a second inner electrode, and the insulating layer and outer electrode may each have a second opening that are coaxially aligned with the second inner electrode. An angioplasty shockwave catheter may have a plurality of such low-profile electrode assemblies along its length to break up calcified plaques along a length of a vessel.

17 Claims, 28 Drawing Sheets

Related U.S. Application Data continuation of application No. 13/831,543, filed on Mar. 14, 2013, now Pat. No. 8,888,788.

(60) Provisional application No. 61/680,033, filed on Aug. 6, 2012.

(52) U.S. Cl.
CPC ............... *A61B 2017/22021* (2013.01); *A61B 2017/22025* (2013.01); *A61B 2017/22028* (2013.01); *A61B 2017/22051* (2013.01); *A61B 2017/22062* (2013.01)

(56) References Cited

U.S. PATENT DOCUMENTS

| | | | |
|---|---|---|---|
| 3,902,499 A | 9/1975 | Shene | |
| 4,027,674 A | 6/1977 | Tessler et al. | |
| 4,662,126 A | 5/1987 | Malcolm | |
| 4,671,254 A | 6/1987 | Fair | |
| 4,685,458 A | 8/1987 | Leckrone | |
| 4,809,682 A | 3/1989 | Forssmann et al. | |
| 4,900,303 A | 2/1990 | Lemelson | |
| 5,009,232 A | 4/1991 | Hassler et al. | |
| 5,057,103 A | 10/1991 | Davis | |
| 5,057,106 A | 10/1991 | Kasevich et al. | |
| 5,078,717 A | 1/1992 | Parins et al. | |
| 5,103,804 A | 4/1992 | Abele et al. | |
| 5,152,767 A | 10/1992 | Sypal et al. | |
| 5,152,768 A | 10/1992 | Bhatta | |
| 5,176,675 A | 1/1993 | Watson et al. | |
| 5,245,988 A | 9/1993 | Einars et al. | |
| 5,246,447 A | 9/1993 | Rosen et al. | |
| 5,281,231 A | 1/1994 | Rosen et al. | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | De La et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | De La et al. | |
| 5,931,805 A | 8/1999 | Brisken | |
| 6,007,530 A | 12/1999 | Doernhoefer et al. | |
| 6,033,371 A | 3/2000 | Torre et al. | |
| 6,083,232 A | 7/2000 | Cox | |
| 6,186,963 B1 | 2/2001 | Schwarze et al. | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | De La Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,740,081 B2 | 5/2004 | Hilal | |
| 6,755,821 B1 | 6/2004 | Fry | |
| 6,989,009 B2 | 1/2006 | Lafontaine | |
| 7,241,295 B2 | 7/2007 | Maguire | |
| 7,505,812 B1 | 3/2009 | Eggers et al. | |
| 7,569,032 B2 | 8/2009 | Naimark et al. | |
| 7,873,404 B1 | 1/2011 | Patton et al. | |
| 8,556,813 B2 | 10/2013 | Cioanta et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 9,005,216 B2 | 4/2015 | Hakala et al. | |
| 9,011,463 B2 | 4/2015 | Adams et al. | |
| 9,333,000 B2 | 5/2016 | Hakala et al. | |
| 9,433,428 B2 | 9/2016 | Hakala et al. | |
| 9,642,673 B2 | 5/2017 | Adams et al. | |
| 2001/0044596 A1 | 11/2001 | Jaafar | |
| 2002/0045890 A1 | 4/2002 | Celliers et al. | |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0010249 A1 | 1/2004 | Truckai et al. | |
| 2004/0044308 A1 | 3/2004 | Naimark et al. | |
| 2004/0097963 A1 | 5/2004 | Seddon et al. | |
| 2004/0097996 A1 | 5/2004 | Rabiner et al. | |
| 2004/0162508 A1 | 8/2004 | Uebelacker et al. | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0113722 A1 | 5/2005 | Schultheiss et al. | |
| 2005/0113822 A1 | 5/2005 | Fuimaono et al. | |
| 2005/0228372 A1 | 10/2005 | Truckai et al. | |
| 2005/0251131 A1 | 11/2005 | Lesh | |
| 2006/0004286 A1 | 1/2006 | Chang et al. | |
| 2006/0069424 A1 | 3/2006 | Acosta et al. | |
| 2006/0184076 A1 | 8/2006 | Gill et al. | |
| 2006/0190022 A1 | 8/2006 | Beyar et al. | |
| 2007/0016112 A1 | 1/2007 | Schultheiss et al. | |
| 2007/0088380 A1 | 4/2007 | Hirszowicz et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2007/0255270 A1 | 11/2007 | Carney | |
| 2007/0282301 A1 | 12/2007 | Segalescu et al. | |
| 2008/0097251 A1 | 4/2008 | Babaev | |
| 2008/0188913 A1 | 8/2008 | Stone et al. | |
| 2009/0041833 A1 | 2/2009 | Bettinger et al. | |
| 2009/0247945 A1 | 10/2009 | Levit et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 | 5/2010 | Hawkins et al. | |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0208185 A1 | 8/2011 | Diamant et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0150874 A1 | 6/2013 | Kassab | |
| 2014/0005576 A1 | 1/2014 | Adams et al. | |
| 2014/0039513 A1 | 2/2014 | Hakala et al. | |
| 2014/0046229 A1 | 2/2014 | Hawkins et al. | |
| 2014/0052145 A1 | 2/2014 | Adams et al. | |
| 2014/0052147 A1 | 2/2014 | Hakala et al. | |
| 2014/0074111 A1 | 3/2014 | Hakala et al. | |
| 2014/0074113 A1 | 3/2014 | Hakala et al. | |
| 2014/0214061 A1 | 7/2014 | Adams et al. | |
| 2014/0243847 A1 | 8/2014 | Hakala et al. | |
| 2014/0288570 A1 | 9/2014 | Adams | |
| 2015/0073430 A1 | 3/2015 | Adams et al. | |
| 2015/0238208 A1 | 8/2015 | Adams et al. | |
| 2015/0320432 A1 | 11/2015 | Adams | |

(56) References Cited

U.S. PATENT DOCUMENTS

| | | | |
|---|---|---|---|
| 2016/0183957 | A1 | 6/2016 | Hakala et al. |
| 2016/0324534 | A1 | 11/2016 | Hawkins et al. |
| 2017/0135709 | A1 | 5/2017 | Nguyen et al. |

FOREIGN PATENT DOCUMENTS

| | | | |
|---|---|---|---|
| CN | 102271748 A | 12/2011 | |
| CN | 102355856 A | 2/2012 | |
| CN | 102765785 A | 11/2012 | |
| DE | 3038445 A1 | 5/1982 | |
| DE | 202006014285 U1 | 12/2006 | |
| EP | 0442199 A2 | 8/1991 | |
| EP | 0571306 A1 | 11/1993 | |
| EP | 0647435 A1 | 4/1995 | |
| JP | 62-275446 A | 11/1987 | |
| JP | 6-125915 A | 5/1994 | |
| JP | 7-47135 A | 2/1995 | |
| JP | 10-99444 A | 4/1998 | |
| JP | 10-513379 A | 12/1998 | |
| JP | 2002-538932 A | 11/2002 | |
| JP | 2004-81374 A | 3/2004 | |
| JP | 2005-501597 A | 1/2005 | |
| JP | 2005-95410 A | 4/2005 | |
| JP | 2005-515825 A | 6/2005 | |
| JP | 2006-516465 A | 7/2006 | |
| JP | 2007-532182 A | 11/2007 | |
| JP | 2011-524203 A | 9/2011 | |
| JP | 2012-508042 A | 4/2012 | |
| WO | 1996/024297 A1 | 8/1996 | |
| WO | 1999/000060 A1 | 1/1999 | |
| WO | 1999/02096 A1 | 1/1999 | |
| WO | 2004/069072 A2 | 8/2004 | |
| WO | 2005/099594 A1 | 10/2005 | |
| WO | 2006/127158 A2 | 11/2006 | |
| WO | 2007/149905 A2 | 12/2007 | |
| WO | 2009/121017 A1 | 10/2009 | |
| WO | 2009/152352 A2 | 12/2009 | |
| WO | 2010/014515 A2 | 2/2010 | |
| WO | 2011/094111 A2 | 8/2011 | |
| WO | 2011/143468 A2 | 11/2011 | |
| WO | 2012/025833 A2 | 3/2012 | |
| WO | 2013/059735 A | 4/2013 | |
| WO | 2015/017499 A1 | 2/2015 | |

OTHER PUBLICATIONS

Final Office Action received for U.S. Appl. No. 13/534,658, dated Aug. 23, 2016, 11 pages.
Intention to Grant received for European Patent Application No. 13756766.5, dated Jan. 8, 2016, 5 pages.
Notice of Allowance received for U.S. Appl. No. 14/218,858, dated Aug. 26, 2016, 8 pages.
Office Action received for Chinese Patent Application No. 201380033808.3, dated Jul. 5, 2016, 9 pages (3 pages of English translation and 6 pages of Official).
Office Action received for Chinese Patent Application No. 201380041656.1, dated Jul. 5, 2016, 9 pages (4 pages of English translation and 5 pages of Official).
Office Action received for Chinese Patent Application No. 201380042887.4, dated Aug. 8, 2016, 9 pages (4 pages of English translation and 5 pages of Official).
Hguyen, Hoa D., Unpublished U.S. Appl. No. 15/346,132, filed Nov. 8, 2016, titled "Shock Wave Electrodes".
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Office Action received for Australian Patent Application No. 2013300176, dated Nov. 10, 2016, 2 pages.
Office Action received for Japanese Patent Application No. 2015-526523, dated Jan. 25, 2017, 8 pages (5 pages of English Translation and 3 pages of Official Only).
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Extended European Search Report (includes Supplementary European Search Report and Search Opinion) received for European Patent Application No. 09763640.1, dated Oct. 10, 2013, 5 pages.
Advisory Action Received for U.S. Appl. No. 12/482,995, dated Jun. 2, 2014, 3 pages.
Advisory Action Received for U.S. Appl. No. 12/482,995, dated Sep. 29, 2011, 2 pages.
Final Office Action received for U.S. Appl. No. 12/482,995, dated Feb. 20, 2014, 11 pages.
Non Final Office Action received for U.S. Appl. No. 12/482,995, dated Aug. 13, 2014, 10 pages.
Non Final Office Action received for U.S. Appl. No. 12/482,995, dated Jul. 12, 2013, 11 pages.
Notice of Allowance received for U.S. Appl. No. 12/482,995, dated Dec. 24, 2014, 6 pages.
Non-Final Office Action received for U.S. Appl. No. 12/501,619, dated Jan. 28, 2014, 10 pages.
Advisory Action Received for U.S. Appl. No. 12/581,295, dated Jul. 3, 2014, 3 pages.
Final Office Action received for U.S. Appl. No. 12/581,295, dated Jun. 5, 2014, 14 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Non Final Office Action received for U.S. Appl. No. 12/611,997, dated Nov. 26, 2014, 8 pages.
Advisory Action Received for U.S. Appl. No. 13/049,199, dated Jun. 7, 2012, 3 pages.
Final Office Action received for U.S. Appl. No. 13/049,199 dated Aug. 11, 2014, 8 pages.
Non-Final Office Action received for U.S. Appl. No. 13/049,199, dated Feb. 4, 2014, 8 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Advisory Action received for U.S. Appl. No. 13/267,383, dated Jan. 6, 2014, 4 pages.
Final Office Action Received for U.S. Appl. No. 13/267,383, dated May 28, 2015, 12 pages.
Final Office Action received for U.S. Appl. No. 13/267,383, dated Oct. 25, 2013, 8 pages.
Non-Final Office Action received for U.S. Appl. No. 13/267,383, dated Feb. 25, 2015, 9 pages.
Non Final Office Action received for U.S. Appl. No. 13/465,264, dated Oct. 29, 2014, 13 pages.
Non-Final Office Action received for U.S. Appl. No. 13/465,264, dated Dec. 23, 2014, 13 pages.
Notice of Allowance received for U.S. Appl. No. 13/465,264, dated May 8, 2015, 7 pages.
Advisory Action received for U.S. Appl. No. 13/615,107, dated Nov. 6, 2015, 3 pages.
Final Office Action received for U.S. Appl. No. 13/615,107 dated Sep. 1, 2015, 9 pages.
Non-Final Office Action received for U.S. Appl. No. 13/615,107, dated Apr. 24, 2015, 9 pages.
Final Office Action received for U.S. Appl. No. 13/646,570, dated Dec. 23, 2014, 10 pages.
Non Final Office Action received for U.S. Appl. No. 13/646,570, dated Oct. 29, 2014, 10 pages.
Notice of Allowance received for U.S. Appl. No. 13/646,570, dated Mar. 11, 2015, 7 pages.
Non-Final Office Action received for U.S. Appl. No. 13/646,583, dated Oct. 31, 2014, 8 pages.

(56) References Cited

OTHER PUBLICATIONS

Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Extended European Search Report received for European Patent Application No. 13827971.6, dated Apr. 12, 2016, 8 pages.
Non-Final Office Action received for U.S. Appl. No. 14/061,554, dated Mar. 12, 2014, 14 pages.
Notice of Allowance received for U.S. Appl. No. 14/061,554, dated Apr. 25, 2014, 8 pages.
Non Final Office Action received for U.S. Appl. No. 14/079,463, dated Mar. 4, 2014, 9 pages.
Notice of Allowance received for U.S. Appl. No. 14/079,463, dated Apr. 1, 2014, 5 pages.
Non-Final Office Action received for U.S. Appl. No. 14/271,276, dated Aug. 4, 2014, 7 pages.
Notice of Allowance received for U.S. Appl. No. 14/271,276, dated Feb. 25, 2015, 8 pages.
Final Office Action received for U.S. Appl. No. 14/271,342 dated Feb. 27, 2015, 7 pages.
Non-Final Office Action received for U.S. Appl. No. 14/271,342, dated Sep. 2, 2014, 6 pages.
Notice of Allowance received for U.S. Appl. No. 14/271,342, dated Mar. 13, 2015, 5 pages.
Non Final Office Action received for U.S. Appl. No. 14/515,130, dated Jan. 14, 2016, 16 pages.
Notice of Allowance received for Canadian Patent Application No. 2,727,429, dated May 26, 2015, 1 page.
Office Action received for Canadian Patent Application No. 2,727,429, dated Apr. 14, 2015, 4 pages.
Notice of Acceptance Received for Australian Patent Application No. 2009257368, dated Aug. 28, 2014, 2 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Decision to Grant received for Japanese Patent Application No. 2011513694, dated Oct. 7, 2014, 3 pages of official only.
Office Action received for Japanese Patent Application No. 2011-513694, dated Aug. 27, 2013, 6 pages (3 pages of English Translation and 3 pages of Official).
Office Action Received for Japanese Patent Application No. 2011-513694, dated Jun. 10, 2014, 4 pages total (2 pages of Official and 2 pages of English Translation).
Office Action Received for Japanese Patent Application No. 2011-534914, dated Jul. 15, 2014, 3 pages (1 page of English Translation and 2 pages of Official).
Office Action Received for Japanese Patent Application No. 2014-158517, dated May 19, 2015, 5 pages (2 pages of English Translation and 3 pages of Official).
International Preliminary Report on Patentability received for PCT Patent Application No. PCT/US2009/047070, dated Dec. 23, 2010, 7 pages.
International Search Report received for PCT Patent Application No. PCT/US2009/047070, dated Jan. 19, 2010, 4 pages.
Written Opinion received for PCT Patent Application No. PCT/US2009/047070, dated Jan. 19, 2010, 5 pages.
International Preliminary Report on Patentability received for PCT Patent Application No. PCT/US2011/047070, dated Feb. 21, 2013, 7 pages.
International Written Opinion received for PCT Patent Application No. PCT/US2011/047070, dated May 1, 2012, 5 pages.
International Preliminary Report on Patentability received for PCT Patent Application No. PCT/US2012/023172, dated Aug. 15, 2013, 6 pages.
International Search Report received for PCT Patent Application No. PCT/US2012/023172, dated Sep. 28, 2012, 3 pages.
Written Opinion received for PCT Patent Application No. PCT/US2012/023172, dated Sep. 28, 2012, 4 pages.
International Preliminary Report on Patentability received for PCT Patent Application No. PCT/US2012/063925, dated May 22, 2014, 12 pages.
International Preliminary Report on Patentability received for PCT Patent Application No. PCT/US2013/031805, dated Feb. 19, 2015, 11 pages.
International Search Report and Written Opinion received for PCT Patent Application No. PCT/US2013/031805 dated May 20, 2013, 13 pages.
International Preliminary Report on Patentability received for PCT Patent Application No. PCT/US2013/039987 dated Nov. 20, 2014, 11 pages.
International Search Report and Written Opinion received for PCT Patent Application No. PCT/US2013/039987, dated Sep. 23, 2013, 15 pages.
International Preliminary Report on Patentability received for PCT Patent Application No. PCT/US2013/048277 dated Jan. 8, 2015, 9 pages.
International Search Report and Written Opinion received for PCT Patent Application No. PCT/US2013/048277, dated Oct. 2, 2013, 14 pages.
International Preliminary Report on Patentability received for PCT Patent Application No. PCT/US2013/055431, dated Feb. 26, 2015, 7 pages.
International Search Report and Written Opinion received for PCT Patent Application No. PCT/US2013/055431, dated Nov. 12, 2013, 9 pages.
International Preliminary Report on Patentability received for PCT Patent Application No. PCT/US2013/059533 dated Mar. 26, 2015, 10 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088 dated Jul. 16, 2015, 13 pages.
Rosenschein et al., "Shock-Wave Thrombus Ablation, a New Method for Noninvasive Mechanical Thrombolysis", The American Journal of Cardiology, vol. 70, pp. 1358-1361.
Zhong et al., "Transient Oscillation of Cavitation Bubbles Near Stone Surface During Electrohydraulic Lithotripsy", Journal of Endourology, vol. 11, No. 1, pp. 55-61.
Cleveland et al., "The Physics of Shock Wave Lithotripsy Extracorporeal Shock Wave Lithotripsy", Part IV, Chapter 38, pp. 317-332.
Connors et al., "Renal Nerves Mediate Changes in Contralateral Renal Blood Flow after Extracorporeal Shockwave Lithotripsy", Nephron Physiol, vol. 95, pp. 67-75.
Gambihler et al., "Permeabilization of the Plasma Membrane of LI210 Mouse Leukemia Cells Using Lithotripter Shock Waves", The Journal of Membrane Biology, vol. 141, pp. 267-275.
Grassi et al., "Novel Antihypertensive Therapies: Renal Sympathetic Nerve Ablation and Carotid Baroreceptor Stimulation", Curr Hypertens Rep, vol. 14, pp. 567-572.
Kodama et al., "Shock wave-mediated molecular delivery into cells", Biochimica et Biophysica Acta, vol. 1542, pp. 186-194.
Lauer et al., "Shock wave permeabilization as a new gene transfer method", Gene Therapy, vol. 4, pp. 710-715.
International Search Report and Written Opinion received for PCT Patent Application No. PCT/US2016/060817, dated Feb. 20, 2017, 13 pages.
Notice of Allowance received for Japanese Patent Application No. 2015-520522, dated Feb. 23, 2017, 3 pages (Official Only) (See Communication under 37 CFR § 1.98(a) (3)).
Notice of Allowance received for Chinese Patent Application No. 201380041656.1, dated Mar. 3, 2017, 4 pages (Official Only) (See Communication under 37 CFR § 1.98(a) (3)).
Office Action received for Australian Patent Application No. 2013284490, dated Jun. 5, 2017, 4 pages.
Non-Final Office Action received for U.S. Appl. No. 14/273,063, dated Jun. 3, 2016, 9 pages.

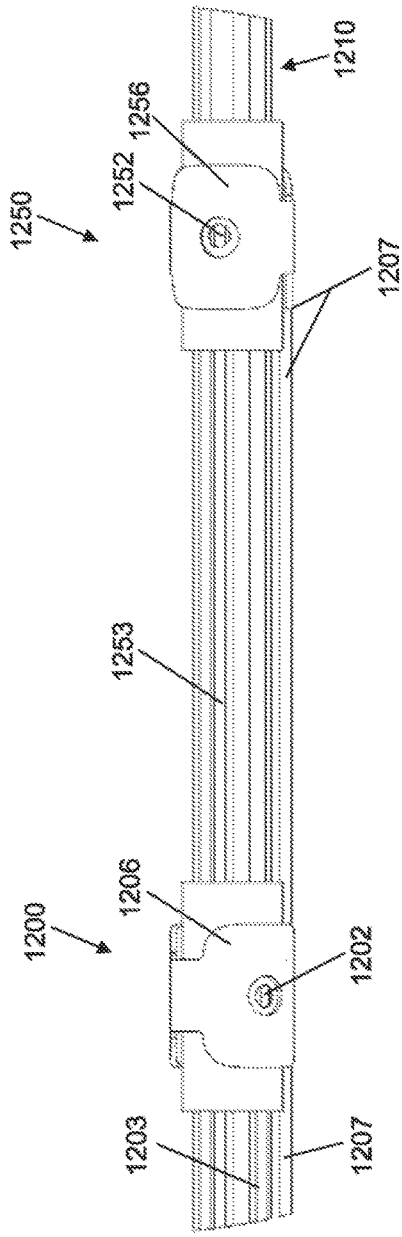
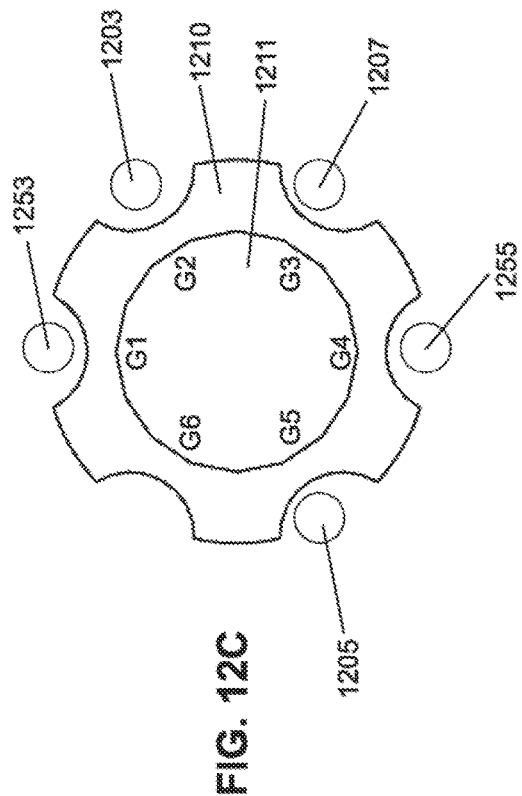
FIG. 12B
FIG. 12C

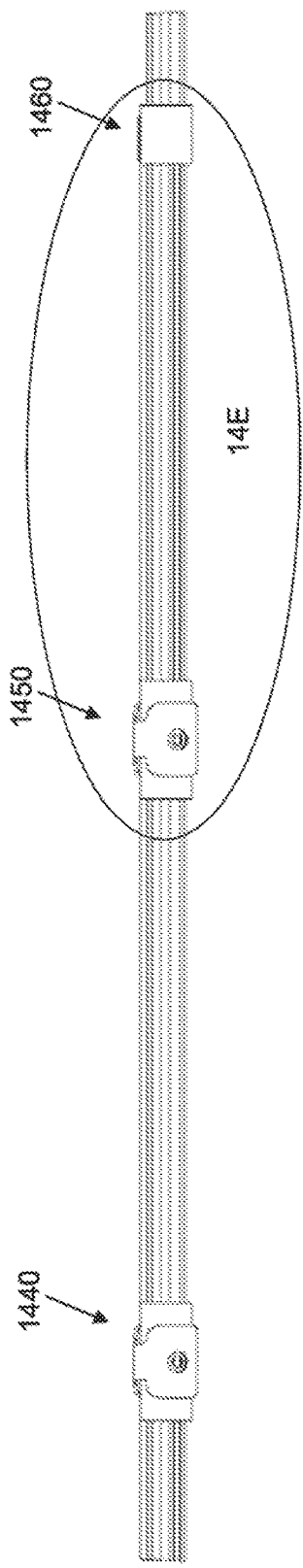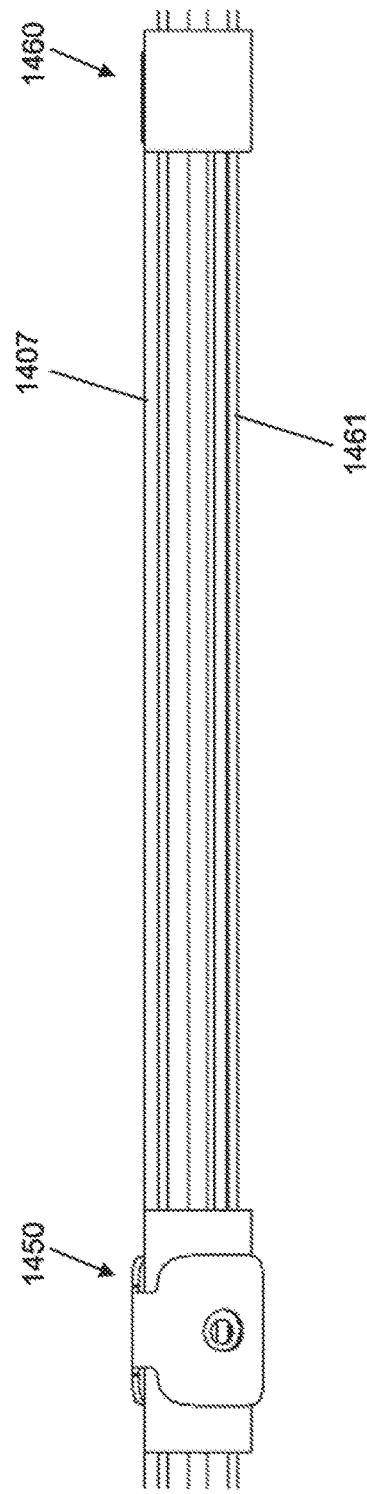

LOW PROFILE ELECTRODES FOR AN ANGIOPLASTY SHOCK WAVE CATHETER

CROSS-REFERENCE TO RELATED APPLICATIONS

This application is a continuation application of U.S. application Ser. No. 14/515,130, entitled LOW PROFILE ELECTRODES FOR AN ANGIOPLASTY SHOCK WAVE CATHETER, filed Oct. 15, 2014, which is a continuation application of U.S. application Ser. No. 13/831,543, filed Mar. 14, 2013, now issued as U.S. Pat. No. 8,888,788, which claims priority to U.S. Provisional Patent Application Ser. No. 61/680,033, filed Aug. 6, 2012, all of which are hereby incorporated by reference in their entirety and for all purposes.

BACKGROUND

Currently, angioplasty balloons are used to open calcified lesions in the wall of an artery. However, as an angioplasty balloon is inflated to expand the lesion in the vascular wall, the inflation pressure stores a tremendous amount of energy in the balloon until the calcified lesion breaks or cracks. That stored energy is then released and may stress and injure the wall of the blood vessel.

Electrohydraulic lithotripsy has been typically used for breaking calcified deposits or "stones" in the urinary or biliary track. Recent work by the assignee shows that lithotripsy electrodes may similarly be useful for breaking calcified plaques in the wall of a vascular structure. Shockwaves generated by lithotripsy electrodes may be used to controllably fracture a calcified lesion to help prevent sudden stress and injury to the vessel or valve wall when it is dilated using a balloon. A method and system for treating stenotic or calcified vessels is described in co-pending U.S. application Ser. No. 12/482,995, filed Jun. 11, 2009. A method and system for treating stenotic or calcified aortic valves is described in co-pending U.S. application Ser. No. 13/534,658, filed Jun. 27, 2012. As described in those applications, a balloon is placed adjacent leaflets of a valve to be treated and is inflatable with a liquid. Within the balloon is a shock wave generator that produces shock waves that propagate through the liquid and impinge upon the valve. The impinging shock waves soften, break and/or loosen the calcified regions for removal or displacement to open the valve or enlarge the valve opening. Additional improved lithotripsy or shockwave electrodes that can readily access and treat various locations in the vasculature for angioplasty and/or valvuloplasty procedures may be desirable.

BRIEF SUMMARY

Described herein are low-profile electrodes for use with an angioplasty shockwave catheter. A low-profile electrode assembly may have an inner electrode, an insulating layer disposed over the inner electrode such that an opening in the insulating layer is aligned with the inner electrode, and an outer electrode disposed over the insulating sheath such that an opening in the outer electrode is coaxially aligned with the opening in the insulating layer. This layered configuration allows for the generation of shockwaves that initiate and/or propagate outward from a side of the catheter. In some variations, the electrode assembly may have at least a second inner electrode, and the insulating layer and outer electrode may each have at least a second opening that are coaxially aligned with the second inner electrode. An angioplasty shockwave catheter may have a plurality of such low-profile electrode assemblies along its length to break up calcified plaques along a length of a vessel.

One variation of a device for generating shockwaves may comprise an axially extending catheter, a balloon surrounding a portion of the catheter, said balloon being fillable with a conductive fluid, an insulating layer wrapped around a portion of the catheter within the balloon, the insulating layer having a first aperture therein, a first inner electrode carried within the catheter and aligned with the first aperture of the insulating layer, and an outer electrode mounted on the insulating layer and having a first aperture coaxially aligned with the first aperture in the insulating layer and arranged so that when the balloon is filled with fluid and a voltage is applied across the electrodes, a first shockwave will be initiated from a first side location of the catheter. The insulating layer may be an insulating sheath and the outer electrode may be in the form of a sheath that is circumferentially mounted around the insulating sheath. The size of the first aperture in the outer electrode may be larger than the size of the first aperture in the insulating sheath. The device may further comprise a first wire and a second wire, where the first and second wires extend along the length of the catheter, and where the first wire may be connected to the first inner electrode, and the second wire may be connected to the outer electrode. In some variations, the catheter may have first and second grooves that extend along the length of the catheter, and the first wire is slidably disposed within the first groove and the second wire is slidably disposed within the second groove. For example, a length of the first and second wires may be partially secured within the first and second grooves. The first inner electrode and the outer electrode may be crimped over an electrically conductive portion of the first and second wires, respectively. In some variations, the first inner electrode may be a hypotube that is crimped over the first wire.

In some variations of a device for generating shockwave, the insulating sheath may have a second aperture circumferentially opposite the first aperture in the insulating sheath and the device may further comprise a second inner electrode aligned with the second aperture in the insulating sheath and the outer electrode sheath may have a second aperture coaxially aligned with the second aperture in the insulating sheath and arranged so that when the balloon is filled with a fluid and a voltage is applied across the second inner electrode and the outer electrode, a second shockwave will be initiated from a second side location of the catheter that is opposite to the first side location. In some variations, the device may comprise a first wire, a second wire, and a third wire, where the first, second and third wires that extend along the length of the catheter, where the first wire is connected to the first inner electrode, the second wire is connected to the outer electrode, and the third wire is connected to the second inner electrode. The catheter may have first, second and third grooves that extend along the length of the catheter, and the first wire may be slidably disposed within the first groove, the second wire may be slidably disposed within the second groove, and the third wire may be slidably disposed within the third groove. The first inner electrode and the second inner electrode may be crimped over an electrically conductive portion of the first and third wires, respectively. The first inner electrode and the second inner electrode may be first and second hypotubes that are each crimped over the first and third wires, respectively. In some variations, the surface of the first and second crimped hypotubes each circumferentially spans a portion of the elongate member. For example, the first and second crimped hypotubes may each circumferentially span at least ⅙ of the way around the circumference of the elongate member.

Optionally, the insulating sheath may have a third aperture circumferentially 90 degrees from the first aperture in the insulating sheath and may further comprise a third inner electrode aligned with the third aperture in the insulating sheath. The outer electrode sheath may have a third aperture coaxially aligned with the third aperture in the insulating sheath and arranged so that when the balloon is filled with a fluid and a voltage is applied across the third inner electrode and the outer electrode, a third shockwave will be initiated from a third side location that is 90 degrees offset from the first side location. In some variations, the insulating sheath may have a fourth aperture circumferentially opposite the third aperture in the insulating sheath and the device may further comprise a fourth inner electrode aligned with the fourth aperture in the insulating sheath. The outer electrode sheath may have a fourth aperture coaxially aligned with the fourth aperture in the insulating sheath and arranged so that when the balloon is filled with a fluid and a voltage is applied across the fourth inner electrode and the outer electrode, a fourth shockwave will be initiated from a fourth side location that is opposite to the third side location.

Another variation of a device for generating shockwaves may comprise an axially extending catheter, a balloon surrounding a portion of the catheter, the balloon being fillable with a conductive fluid, a first inner electrode mounted on the side of the catheter, an insulating layer having an aperture disposed over the first inner electrode such that the aperture is coaxially aligned with the first inner electrode, and an outer electrode having an aperture disposed over insulating layer such that the outer electrode aperture is coaxially aligned with the insulating layer aperture. In some variations, the first inner electrode, insulating layer and outer electrode do not protrude more than 0.015 inch from the outer surface of the catheter. The device may further comprise a second inner electrode mounted on the side of the catheter at a location that is circumferentially opposite to the first inner electrode, where the insulating layer may have a second aperture coaxially aligned with the second inner electrode and the outer electrode may have a second aperture that is coaxially aligned with the second aperture of the insulating layer.

One variation of a system for generating shockwaves may comprise an axially extending catheter, a balloon surrounding a portion of the catheter, the balloon being fillable with a conductive fluid, a first electrode assembly at a first location along the length of the catheter, the first electrode assembly comprising a first inner electrode, a second inner electrode, and an outer electrode and configured to initiate shockwaves at two circumferentially opposite locations, a second electrode assembly at a second location along the length of the catheter, the second electrode assembly comprising a first inner electrode, a second inner electrode, and an outer electrode and configured to initiate shockwaves at two circumferentially opposite locations, a third electrode assembly at a third location along the length of the catheter, the third electrode assembly comprising a first inner electrode, a second inner electrode, and an outer electrode and configured to initiate shockwaves at two circumferentially opposite locations, a fourth electrode assembly at a fourth location along the length of the catheter, the fourth electrode assembly comprising a first inner electrode, a second inner electrode, and an outer electrode and configured to initiate shockwaves at two circumferentially opposite locations, a fifth electrode assembly at a fifth location along the length of the catheter, the fifth electrode assembly comprising a first inner electrode, a second inner electrode, and an outer electrode and configured to initiate shockwaves at two circumferentially opposite locations, and a voltage pulse generator, where the channels of the voltage pulse generator are connected to one or more of the electrode assemblies. In some variations, the first inner electrode of the first electrode assembly may be connected is a first output of the voltage pulse generator, the second inner electrode of the first electrode assembly may be connected to the first inner electrode of the second electrode assembly, the first inner electrode of the third electrode assembly may be connected to a second output of the voltage pulse generator, the second inner electrode of the third electrode assembly may be connected to a third output of the voltage pulse generator, the first inner electrode of the fourth electrode assembly may be connected to a fourth output of the voltage pulse generator, the second inner electrode of the fourth electrode assembly may be connected to the first inner electrode of the fifth electrode assembly, and the second inner electrode of the second electrode assembly, the outer electrode of the third electrode assembly, and the second inner electrode of the fifth electrode assembly may all be connected to a fifth output of the voltage pulse generator.

Another variation of a device for generating shockwaves may comprise an elongate member, a first electrode assembly located along the side of the elongate member at a first longitudinal location, where the first electrode assembly is configured to initiate shockwaves at a first side location on the elongate member, a second electrode assembly circumferentially opposite the first electrode assembly, where the second electrode assembly is configured to initiate shockwaves at a second side location that is circumferentially opposite the first side location of the elongate member, and a balloon surrounding a portion of the elongate member, the balloon being fillable with a conductive fluid.

Another variation of a system for generating shockwaves may comprise a high voltage pulse generator having a plurality of high voltage output channels, a catheter, a plurality of shockwave sources located along a length of the catheter, where the number of high voltage output channels driving the plurality of shockwave sources is less than the number of shockwave sources, and a balloon surrounding the length of the catheter that has the shockwave sources, the balloon being fillable with a conductive fluid.

BRIEF DESCRIPTION OF THE DRAWINGS

FIGS. 12B and 12C depict the connectivity between the inner electrodes and outer electrodes to attain the configuration of FIG. 12A.

FIGS. 14B-14G depict the connectivity between the inner electrodes and outer electrodes and intermediate nodes (e.g., a distal marker band) to attain the configuration of FIG. 14A.

DETAILED DESCRIPTION

Described herein are devices and systems that comprise one or more low-profile lithotripsy or shockwave electrodes that may be suitable for use in angioplasty and/or valvuloplasty procedures. Lithotripsy or shockwave electrodes may be sealed within an angioplasty or valvuloplasty balloon that is inflated with a fluid (e.g., saline and/or imaging contrast agent). A shockwave electrode may be attached to a source of high voltage pulses, ranging from 100 to 10,000 volts for various pulse durations. This may generate a gas bubble at the surface of the electrode causing a plasma arc of electric current to traverse the bubble and create a rapidly expanding and collapsing bubble, which in turn creates a mechanical shockwave in the balloon. Shockwaves may be mechanically conducted through the fluid and through the balloon to apply mechanical force or pressure to break apart any calcified plaques on, or in, the vasculature walls. The size, rate of expansion and collapse of the bubble (and therefore, the magnitude, duration, and distribution of the mechanical force) may vary based on the magnitude and duration of the voltage pulse, as well as the distance between a shockwave electrode and the return electrode. Shockwave electrodes may be made of materials that can withstand high voltage levels and intense mechanical forces (e.g., about 1000-2000 psi or 20-200 ATM in a few microseconds) that are generated during use. For example, shockwave electrodes may be made of stainless steel, tungsten, nickel, iron, steel, and the like.

Figure 1:
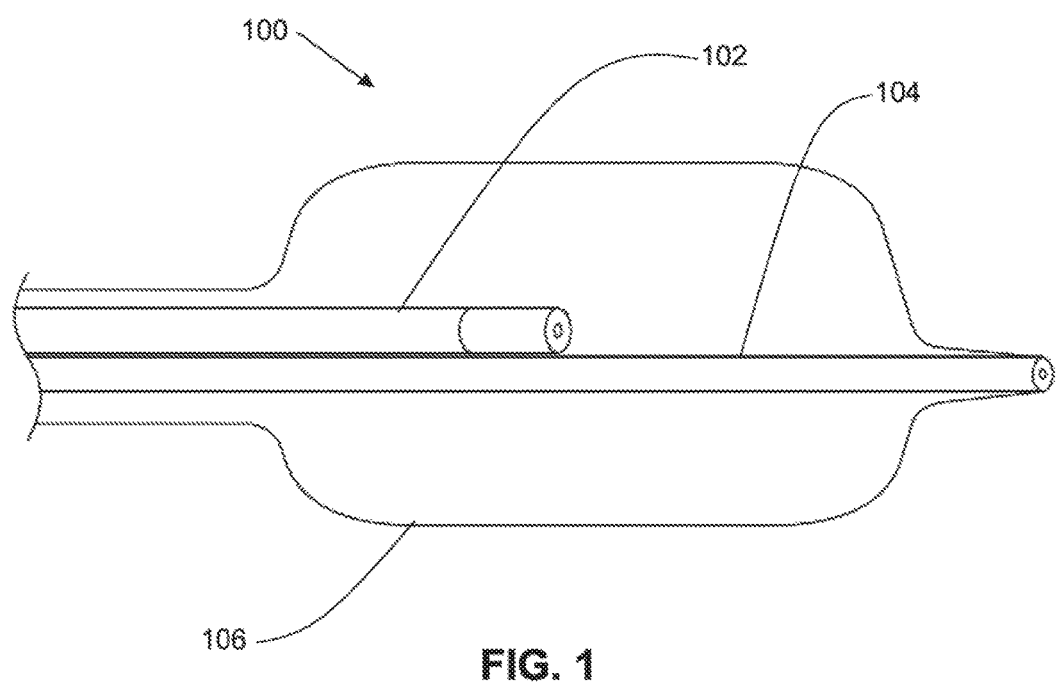
FIG. 1 depicts a shockwave angioplasty device developed by the assignee.

Traditional coaxial shockwave electrodes may be suitable for use in an angioplasty or valvuloplasty balloon, however, when paired in conjunction with a catheter having a guide wire lumen, the crossing profile (i.e., cross-sectional area) may be too large to navigate through and access certain regions of the vasculature. FIG. 1 depicting an example of a shockwave assembly 100 comprising a balloon 106, a coaxial electrode 102 attached in parallel with a catheter 104. For example, a coaxial electrode 102 may have a cross-sectional diameter of about 0.025 inch to about 0.065 inch, and a catheter 104 may have a cross-sectional diameter of about 0.035 inch, which would result in the assembly 100 having a total cross-sectional diameter of at least about 0.06 inch. Such a large crossing profile may limit the ability of the shockwave system to treat tortuous vascular areas and also limit the number of patients that may be treated. Described herein are low-profile shockwave electrodes that may be located along the outer surface of an elongate member (such as a catheter having a guide wire lumen) that do not protrude more than 0.015 inch from the outer surface of the elongate member. For example, the low-profile shockwave electrodes described below may increase the crossing-profile of the elongate member by only about 0.005 inch to about 0.015 inch, thereby minimally affecting the ability of the elongate member to access and treat target vascular tissue.

Also described herein are shockwave devices with a plurality of electrodes along the side of an elongate member that are sealably enclosed in a balloon (i.e., sealed in an enclosed balloon). Since the magnitude, duration and distribution of the mechanical force impinging on a portion of tissue depends at least in part on the location and distance between the shockwave source and the tissue portion, a shockwave device having multiple shockwave electrodes at various locations along the length of the elongate member may help to provide consistent or uniform mechanical force to a region of tissue. The plurality of electrodes may be distributed across the device (e.g., along a longitudinal length of the elongate member) to minimize the distance between the shockwave source(s) and the tissue location being treated. For example, a calcified region of a vein or artery may extend over some longitudinal distance of the vein or artery, and a point source shockwave electrode would not be effective across the full extent of the calcified region because of the varying distance from the shockwave source to the various portions of the calcified region. Described herein are shockwave devices that comprise a plurality of low-profile shockwave electrodes located along a longitudinal length of an elongate member to distribute shockwaves across a length of calcified plaque. The low-profile shockwave electrodes may be located along the circumference of an elongate member. The elongate member may also be sized and shaped to distribute shockwave forces to a non-linear anatomical region. For example, the elongate member may be curved, having a radius of curvature that approximates the radius of curvature of a valve (e.g., an aortic valve). A shockwave device with a curved elongate member may be suitable for applying shockwaves to break calcified plaques in the vicinity of a valve and/or valve leaflets as part of a valvuloplasty procedure.

One variation of a low-profile shockwave electrode assembly may comprise a first electrode, a second electrode stacked over the first electrode, and an insulating layer between them. Stacking the second electrode over the first electrode may form a layered electrode assembly that may be formed on the side of a catheter without substantially increasing the cross-sectional profile of the catheter. A stacked or layered electrode assembly located on the side of a catheter may also be able to generate shockwaves that propagate from the side of the catheter without perpendicularly protruding from the catheter (which would increase the cross-sectional profile of the catheter). The insulating layer may have a first opening and the second electrode may have a second opening that is coaxially aligned with the first opening. Coaxial alignment between the first opening in the insulating layer and the second opening in the second electrode may comprise aligning the center of each of the openings along the same axis. The opening in the insulating layer and the opening in the second electrode may be concentric, such that the center of the insulating layer opening is aligned with the center of the second electrode opening. In some variations, a shockwave device may comprise an elongate member (such as a catheter) and a shockwave electrode assembly having a first electrode that is substantially co-planar with the outer surface of the elongate member. For example, the first electrode may be a pronged electrode that is inserted into the elongate member and connected to a high voltage source via wires within the elongate member. Alternatively, the first electrode may be a hypotube crimped to an electrically conductive portion of a wire, where the wire is located within a longitudinal channel or groove of the elongate member. The wire may have one or more electrically insulated portions and one or more electrically conductive portions, where the conductive portions may align with a first opening of the insulating layer and a second opening of the second electrode. The insulating layer may be a sheet or sheath that wraps at least partially around the circumference of the elongate member and overlaps the first electrode. The insulating layer may overlap the first electrode such that the first electrode is electrically isolated from the environment external to the elongate member but for the opening in the insulating layer. The second electrode may be a ring, sheet, or sheath having a second opening that stacks and/or overlaps with the insulating layer such that the second opening is coaxially aligned with the first opening of the insulating layer. The second electrode may be circumferentially wrapped over the insulating layer. Stacking the first electrode, insulating layer, and second electrode along the outer surface of the elongate member may allow for a shockwave electrode assembly to have a low profile with respect to the elongate member, and coaxially aligning the opening of the insulating layer with the opening of the second electrode may allow for the generation of shockwaves that propagate from the side of the elongate member.

Figure 2:
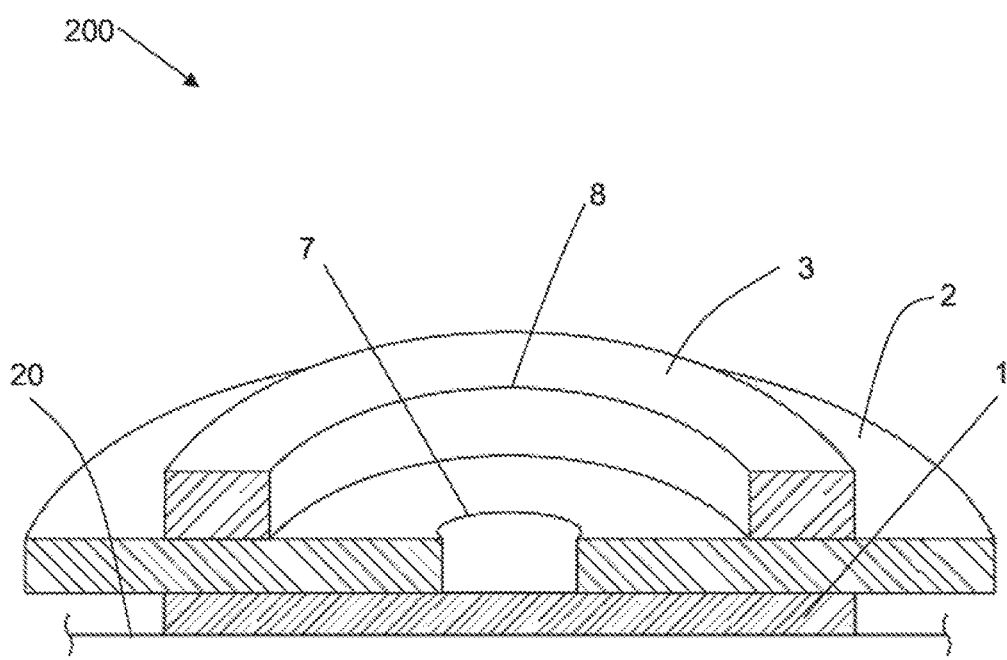
FIG. 2 is a cross-sectional view of a low-profile electrode.

One example of a low-profile shockwave electrode assembly is depicted in FIG. 2. FIG. 2 depicts a cut away perspective view of a low-profile coaxial shockwave electrode assembly 200 that may be located on an elongate member 20 (e.g., a catheter) and enclosed in a balloon (e.g., an angioplasty or valvuloplasty balloon). The electrode assembly 200 may comprise a first electrode 1, an insulating layer 2 overlaying the first electrode, and a second electrode 3. The first electrode 1 may be a positive electrode and the second electrode 3 may be a negative electrode (or vice versa). The elongate member 20 may have a guide wire lumen extending along a length of its longitudinal axis. The first electrode 1 may have a thickness from about 0.001 inch to about 0.01 inch, e.g., 0.002 inch, and may be attached along the outer surface of the elongate member 20. The insulating layer 2 may be made of any material with a high breakdown voltage, such as Kapton, ceramic, polyimide or Teflon. The insulating layer 2 may be about 0.001 inch to about 0.006 inch, e.g., 0.0015 inch, 0.0025 inch, and may have an opening 7 that is aligned over the first electrode 1. Although the second electrode 3 is depicted as having a ring shape, it should be understood that the second electrode may be a planar sheet or layer. The second electrode 3 may have a central opening 8 and stacked over the insulating layer 2 such that the second electrode opening 8 is coaxially aligned with the insulating layer opening 7. The openings 7, 8 may be in the shape of a circle, oval, ellipse, rectangular, or any desired shape. The second electrode 3 may have a thickness from about 0.001 inch to about 0.015 inch, e.g., 0.0025 inch, 0.004 inch. The total thickness of the shockwave electrode assembly 200 may be from about 0.002 inch to about 0.03 inch e.g., 0.005 inch, 0.007 inch, 0.008 inch. Layering and stacking the first electrode, insulating layer and second electrode as depicted in FIG. 2 maintains a substantially flat profile against the outer surface of the elongate member, while maintaining a coaxial electrode configuration for efficient shockwave production. That is, such a configuration may be electrically similar to a traditional coaxial lithotripsy assembly having an inner electrode and an outer electrode surrounding the inner electrode, but without substantially increasing the crossing profile of the elongate member. For example, electrode assembly 200 may have a small enough thickness such that it does not extend more than 0.015 inch from the outer diameter of the elongate member 20. By applying a high voltage pulse between first electrode 1 and second electrode 3 in a fluid filled balloon that encloses the shockwave electrode assembly, an electrohydraulic shockwave can be generated that propagates outward from the side of the elongate member 20. The gap that the current must cross may be at least partially determined by the size and location of the opening 7 in the insulating layer 2 and the size and location of the opening 8 in the second electrode 3. For example, the opening 7 in the insulating layer may be larger than the opening 8 in the second electrode. The opening 7 in the insulating layer may have a diameter from about 0.004 inch to about 0.010 inch, e.g., about 0.008 inch, and the opening 8 in the second electrode may have a diameter from about 0.010 inch to about 0.02 inch, e.g., about 0.012 inch, 0.016 inch, 0.018 inch. The ratio of the diameters between the openings 7, 8 may be varied to adjust the force and duration of the generated shockwave. In some variations, the ratio between the diameter of the opening 7 in the insulating layer and the diameter of the opening 8 in the second electrode may be about 0.5, e.g., 0.56. In some variations, the gap between the openings 7, 8 may be related to the thickness of the insulating layer. For example, the gap between the openings may be 0.5*(diameter of opening 8−diameter of opening 7)+thickness of the insulating layer 2. The desired gap size may vary according to the magnitude of the high voltage pulse applied to the first electrode 1. For example, a gap of about 0.004 inch to about 0.006 inch may be effective for shockwave generation using voltage pulses of about 3,000 V.

Figure 3A:
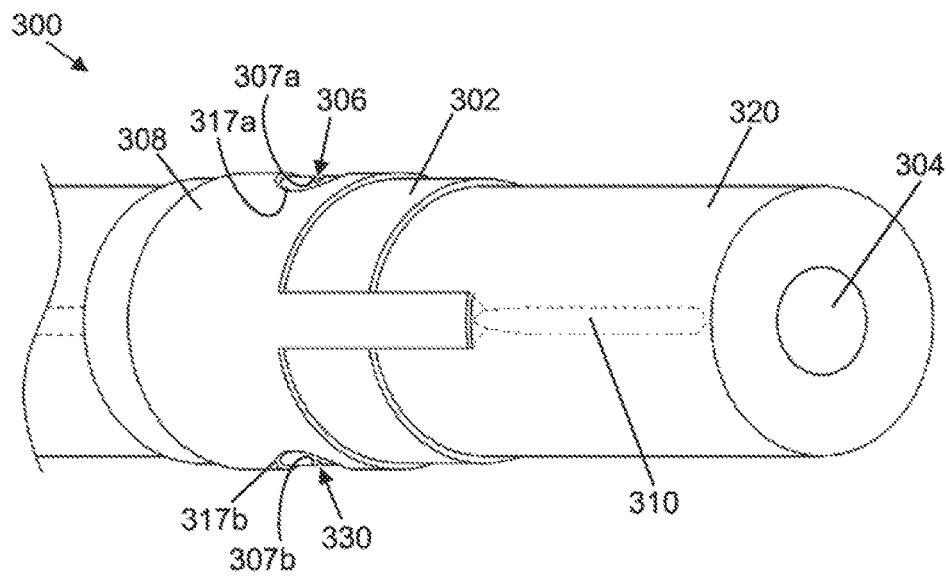
FIGS. 3A-3E schematically depicts the assembly of another variation of a low-profile electrode.
Figure 3B:
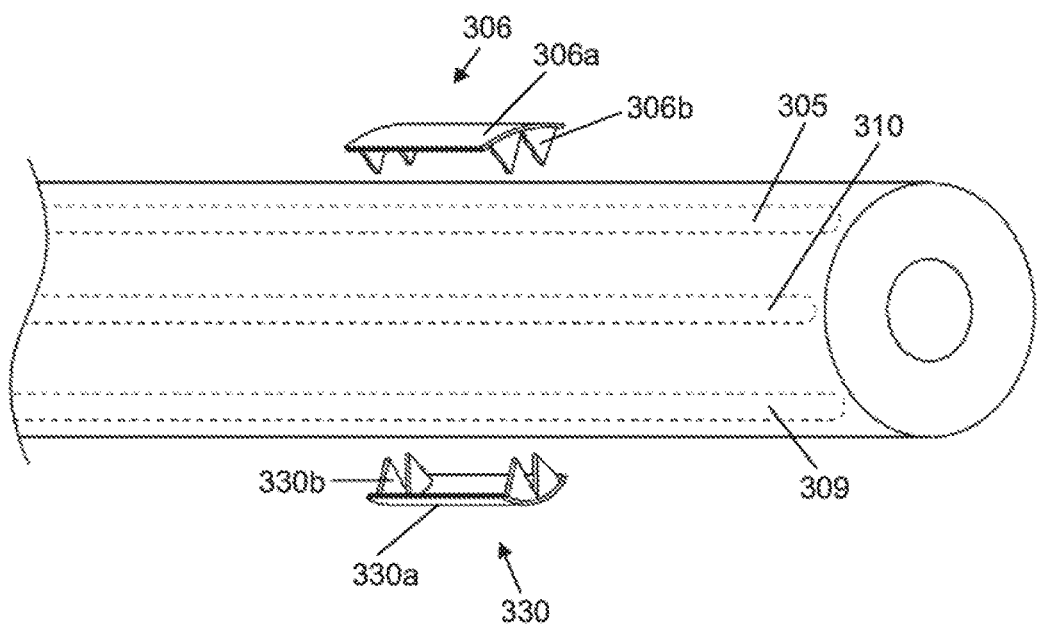

Another variation of a layered or stacked shockwave electrode assembly may comprise an inner electrode located along or recessed within the outer surface of an elongate member, an insulating layer or sheath that circumferentially wraps the elongate member, and an outer electrode that circumferentially wraps around the elongate member and over the insulating sheath. For example, the first electrode may be pressed into the outer surface of the elongate member, and attached to the elongate member by an adhesive (e.g., a conductive adhesive such as conductive epoxy), crimping, welding, and/or pinching. FIGS. 3A-3E depict one variation of a low profile shockwave device 300 comprising an elongate member 320, an inner electrode 306 pressed into and/or recessed within the outer wall of the elongate member 320, an insulating layer 302 disposed over the first electrode 306 such that a first opening 307a in the insulating layer is located over the first electrode, and an outer electrode 308 disposed over the insulating layer 302 such that a first opening 317a in the outer electrode is coaxially aligned with the first opening 307a in the insulating layer. The insulating layer 302 and the outer electrode 308 may each be in the form of a sheath or band, where the insulating sheath may be placed and/or wrapped over the inner electrode and the second electrode sheath may be placed and/or wrapped over the insulating sheath such that the openings in the insulating sheath and outer electrode sheath are coaxially aligned. In some variations, the openings in the insulating sheath and outer electrode sheath are circular and are coaxially aligned such that the centers of the openings are aligned along the same axis and/or concentric. The insulating layer, outer electrode, and second inner electrode may be stacked such that the center of the first opening in the insulating layer, the center of the first opening in the outer electrode, and the first inner electrode are aligned on the same axis. The elongate member may comprise a longitudinal lumen 304 along at least a portion of its length, where the lumen 304 may be configured for passing various instruments and/or a guide wire therethrough. In some variations, the elongate member may be a catheter with a guide wire lumen. The elongate member may also comprise one or more conductors that may extend along the length of the elongate member to connect the inner and/or outer electrode to a high voltage pulse generator. For example, the elongate member may comprise a first wire 305 and a second wire 310 that may be extruded within the walls of the elongate member 320, as depicted in FIG. 3B. Alternatively, the wires could be located in additional longitudinal lumens of the elongate member and/or be located in longitudinal grooves along the outer surface of the elongate member. The wires 305 and 310 may be surrounded by the insulating material of the elongate member and are therefore electrically insulated from each other. Alternatively or additionally, the wires may each have insulating sleeves that wrap around them. The conductive portion of the wires may be exposed at certain locations along its length to contact the inner and outer electrodes. The wires may contact the inner and outer electrodes by soldering, crimping, stapling, pinching, welding, conductive adhesive (e.g., using conductive epoxy), and the like, as further described below. In some variations, the inner electrode may be a hypotube that is crimped to the wire. The connectivity between the conductors and the inner and outer electrodes may be such that the inner electrode is the positive terminal and the outer electrode is the negative terminal (or vice versa). Such a configuration may allow a shockwave generated between the inner and outer electrodes to propagate outward from the side of the elongate member.

Optionally, a shockwave device may have more than one low-profile electrode assembly along the side of the elongate member. In some variations, a first electrode assembly may be located along a side of the elongate member while a second electrode assembly may be located on the opposite side of the elongate member (i.e., 180 degrees from each other). For example and as depicted in FIGS. 3A-3E, the shockwave device 300 may comprise a second inner electrode 330 pressed into and/or recessed within the outer wall of the elongate member 320, opposite the first electrode 306. The elongate member may further comprise a third wire 309 to connect the second inner electrode 330 to a high voltage pulse generator. The insulating layer 302 and the outer electrode may each have an additional opening 307b, 317b (respectively) that are coaxially aligned with each other and with the second inner electrode 330. The insulating layer, outer electrode, and second inner electrode may be stacked such that the center of the second opening in the insulating layer, the center of the second opening in the outer electrode, and the second inner electrode are aligned on the same axis. The first electrode assembly 340 may comprise the first inner electrode 306, the insulating layer 302 with the first opening 307a aligned over the first inner electrode, and the outer electrode 308 with the first opening 317a coaxially aligned with the first opening 307a of the insulating layer. The second electrode assembly 350 may comprise the second inner electrode 330, the insulating layer 302 with the second opening 307b aligned over the second inner electrode, and the outer electrode 308 with the second opening 317b coaxially aligned with the second opening 307b of the insulating layer. By sharing the same insulating layer 320, the first coaxial electrode assembly and the second coaxial electrode assembly may be located at the same longitudinal position along the elongate member. A shockwave device comprising two or more low-profile electrode assemblies located at the same longitudinal position may allow for shockwaves to propagate outward from the elongate member with various angular spread (e.g., up to 360 degree angular spread). For example, a first shockwave generated by the first electrode assembly may propagate outward with an angular spread of about 180 degrees around the elongate member and a second shockwave generated by the second electrode assembly located opposite the first electrode assembly (e.g., 180 degrees from the first electrode assembly) may propagate outward with an angular spread of about 180 degrees around the other side of elongate member, for a cumulative spread of 360 degrees around the elongate member. In other variations, a shockwave device may comprise three or more electrode assemblies, where the three or more electrode assemblies may also be located at the same longitudinal location, but located at different circumferential locations. For example, there may be an additional third electrode and fourth inner electrode around the circumference of the elongate member. The insulating layer may have additional openings aligned over the additional third and fourth inner electrodes, and the outer electrode may have additional openings aligned over the openings of the insulating layer. The third and fourth electrode assemblies formed by the third and fourth inner electrodes and the additional openings in the insulating layer and outer electrode may allow for the generation of four shockwaves from the same longitudinal location along the elongate member. For example, the first, second, third and fourth electrode assemblies may be at the same position along the length of the elongate member, but be circumferentially distributed around the elongate member 90 degrees apart from each other (i.e., the first electrode assembly may be at position 0 degrees, the second electrode assembly may be a position 180 degrees, the third electrode assembly may be at position 90 degrees, and the fourth electrode assembly may be at 270 degrees). This may give rise to four shockwaves that propagate outward, each fanning out with an angular spread of about 90 degrees. The assembly of a shockwave device with two low-profile electrode assemblies at the same position along the length of the elongate member is described below, but it should be understood that similar methods may be used to assemble shockwave devices with three or more low-profile electrode assemblies at the same longitudinal position along the length of the elongate member.

Figure 3C:
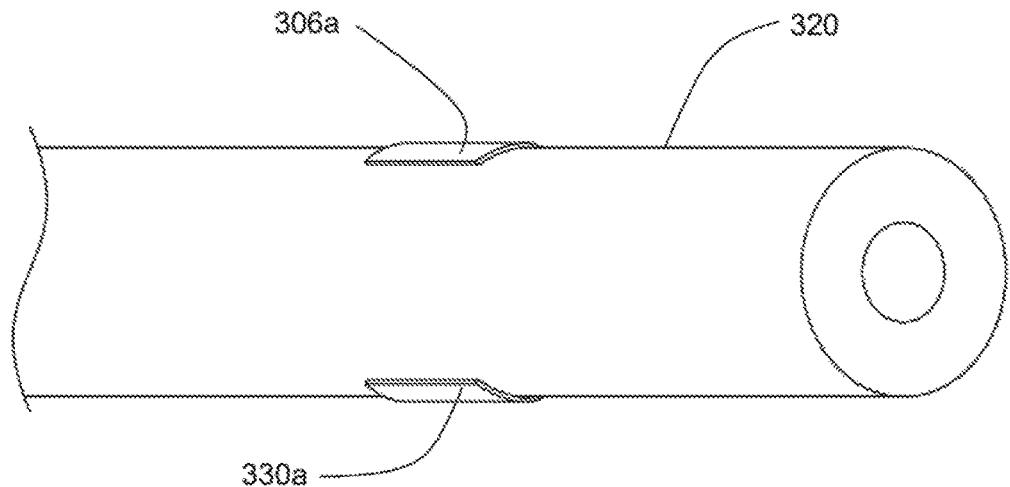

As depicted in FIG. 3B, the first inner and second inner electrodes 306, 330 may be pronged electrodes 306a, 330a and may be shaped to be pressed into the wall of the insulating material of the elongate member. Electrical contact between the first inner and second inner electrodes and the first and third wires may be attained via finger extensions of the pronged electrodes. The pronged electrodes 306a, 330a may have finger extensions 306b, 330b that pinch the first and third wires 305, 309 (respectively) in the wedge of the fingers. The pronged electrodes may also be electrically connected to the wires by any suitable method, for example, soldering, crimping, welding, conductive adhesives (e.g., using conductive epoxies), pressure fit, interference fit, etc. FIG. 3C depicts the first inner and second inner electrode pressed into the side of the elongate member such that the first inner electrode and second inner electrode make electrical contact with the first and third wires within the elongate member. The pronged electrodes 306a, 330a may form the first layer of a stacked low-profile shockwave electrode assembly (e.g., similar to the layered or stacked configuration of the electrode assembly depicted in FIG. 2). The pronged electrodes may comprise tungsten, stainless steel, platinum iridium, nickel, iron, steel, and/or other electrically conductive material.

Figure 3D:
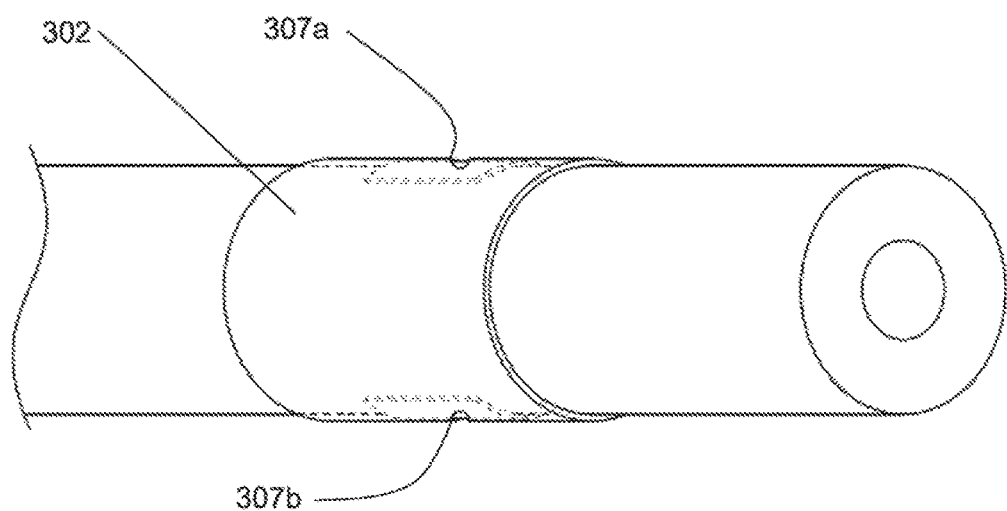

The insulating sheath 302 may circumferentially wrap around the elongate member 320 such that it overlaps with and overlays the first inner electrode and second inner electrode, as depicted in FIG. 3D. The insulating sheath 302 may overlap and stack on top of the first inner electrode and second inner electrode 306 and 330 such that the first opening 307a is coaxially aligned with the first inner electrode and the second opening 307b is aligned with the second inner electrode. The insulating sheath 302 may be made of any material that has a high breakdown voltage, such as Kapton, polyimide, ceramic, Teflon, or any combination of such materials. The insulating sheath 302 may be placed over the elongate member by sliding it from one end of the elongate member to the desired location. The insulating sheath 302 may be secured in the desired location by friction fit, adhesive, welding, crimping, or any other suitable method.

Figure 3E:
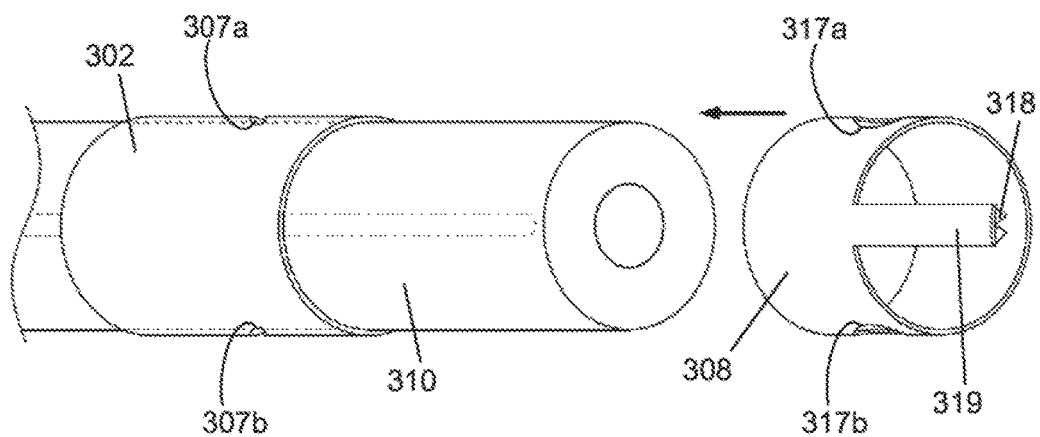

The outer electrode 308 may be a sheath or band that may be configured to stack on top of and/or wrap over the insulating layer 302, as shown in FIG. 3E. The outer electrode 308 may have an extension 319 with pointed fingers 318 configured to penetrate the elongate member to contact the second wire 310 (e.g., by crimping the fingers 318 so that the fingers are pressed into and on the wire 310). The outer electrode 308 may be a metallic sheath or band that may wrap or enclose the elongate member. The outer electrode 308 may be positioned such that the first opening 317a is coaxially aligned with the first opening 307a of the insulating sheath 302 and the second opening 317b is coaxially aligned with the second opening 307b of the insulating sheath. In some variations, the outer electrode 308 may be slid over one end of the elongate member and moved longitudinally into the desired position, after which it may be secured by friction fit, conductive adhesive (e.g., using conductive epoxy), welding, soldering, crimping, or any other suitable method. The outer electrode 308 may be made of copper, stainless steel, platinum/iridium or other electrically conductive materials.

As described above, the first inner electrode may be connected to the first wire 305 and the second inner electrode may be connected to the third wire 309. In some variations, the high voltage pulse generator may drive the first wire 305 and third wire 309 together or independently. For example, the pulse generator may apply voltage pulses simultaneously to both wires, and/or may apply voltage pulses sequentially (e.g., a voltage pulse is applied to the first wire without applying a pulse to the third wire, or vice versa). The voltage pulses applied to the third wire may be delayed with respect to the voltage pulses applied to the first wire. In some variations, a multiplexor may be used with the high voltage pulse generator to control application of pulses between the first and third wires. This may allow shockwaves with different frequency, magnitude, and timing to be generated on either side of the elongate member. For example, in some procedures it may be desirable to apply shockwaves on one side of the elongate member but not on the other side (e.g., in an angioplasty procedure where there is a calcified lesion in one portion of the vessel but not in other portions of the vessel). The first, second, and third wires may be directly connected to a high voltage pulse generator, or may first connect to a connector that is then plugged into the high voltage pulse generator.

Figure 4:
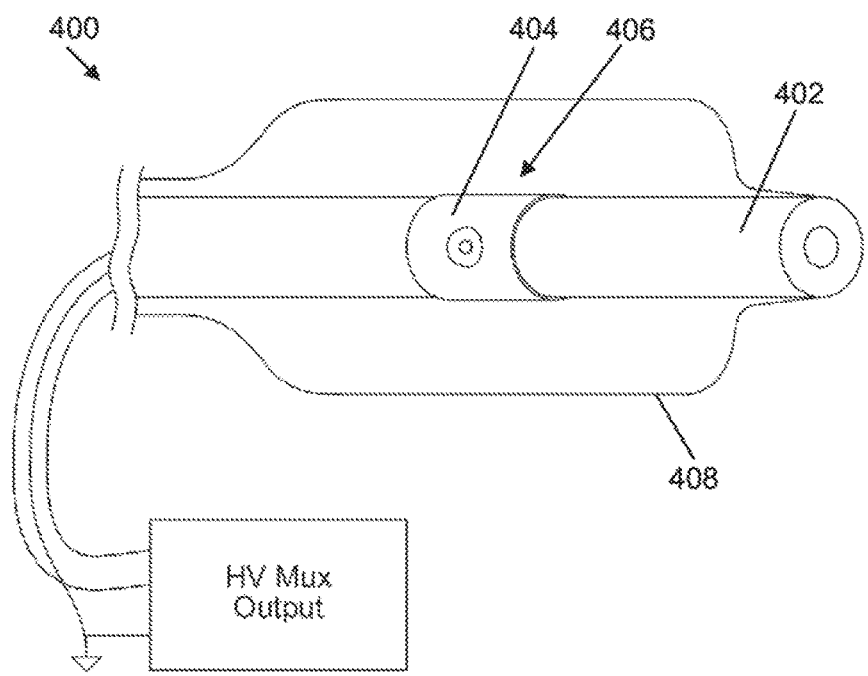
FIG. 4 depicts one variation of a shockwave angioplasty device.

One example of a shockwave device comprising one or more of the low-profile electrode assemblies described above is depicted in FIG. 4. The shockwave device depicted there may be suitable for use in an angioplasty or valvuloplasty procedure. Shockwave device 400 may comprise a catheter 402, a first low-profile coaxial electrode assembly 404, a second low-profile coaxial electrode assembly 406 (not visible in this view), and a balloon 408 enclosing the portion of the elongate member where the first and second electrode assemblies are located. The balloon may be made of an electrically insulating material that may be rigid (e.g., PET, etc.), semi-rigid (e.g., PBAX, nylon, PEBA, polyethylene, etc.), or flexible (e.g., polyurethane, silicone, etc.). The first and second electrode assemblies may be located radially across from each other such that the shockwaves they each generate propagate in opposite directions. The shockwaves generated by each of the electrode assemblies may propagate outward, with an angular spread of 180 degrees. The inner electrodes of each of the electrode assemblies may be connected to conductors within the catheter 402, which may be connect to a high voltage pulse generator. In some variations, the high voltage pulse generator may be a 2 kV to 6 kV, e.g., 3 kV, pulsed power supply. The inner electrode of the first electrode assembly may be connected to a first positive lead of the pulse generator while the inner electrode of the second electrode assembly may be connected to a second positive lead of the pulse generator. The outer electrode may be connected to a negative lead of the pulse generator, or to ground. The first and second positive leads of the pulse generator may be pulsed simultaneously or separately, and may be controlled together or separately controlled (e.g. using a multiplexor), as described previously.

Additional low-profile shockwave electrode assemblies may alternatively or additionally be located along a plurality of locations along the length of the elongate member. For example, the low-profile coaxial shockwave electrode assemblies described above may be linearly arranged along the longitudinal length of the elongate member. Additional variations of shockwave devices with a plurality of electrode assemblies are described below.

Figure 5A:
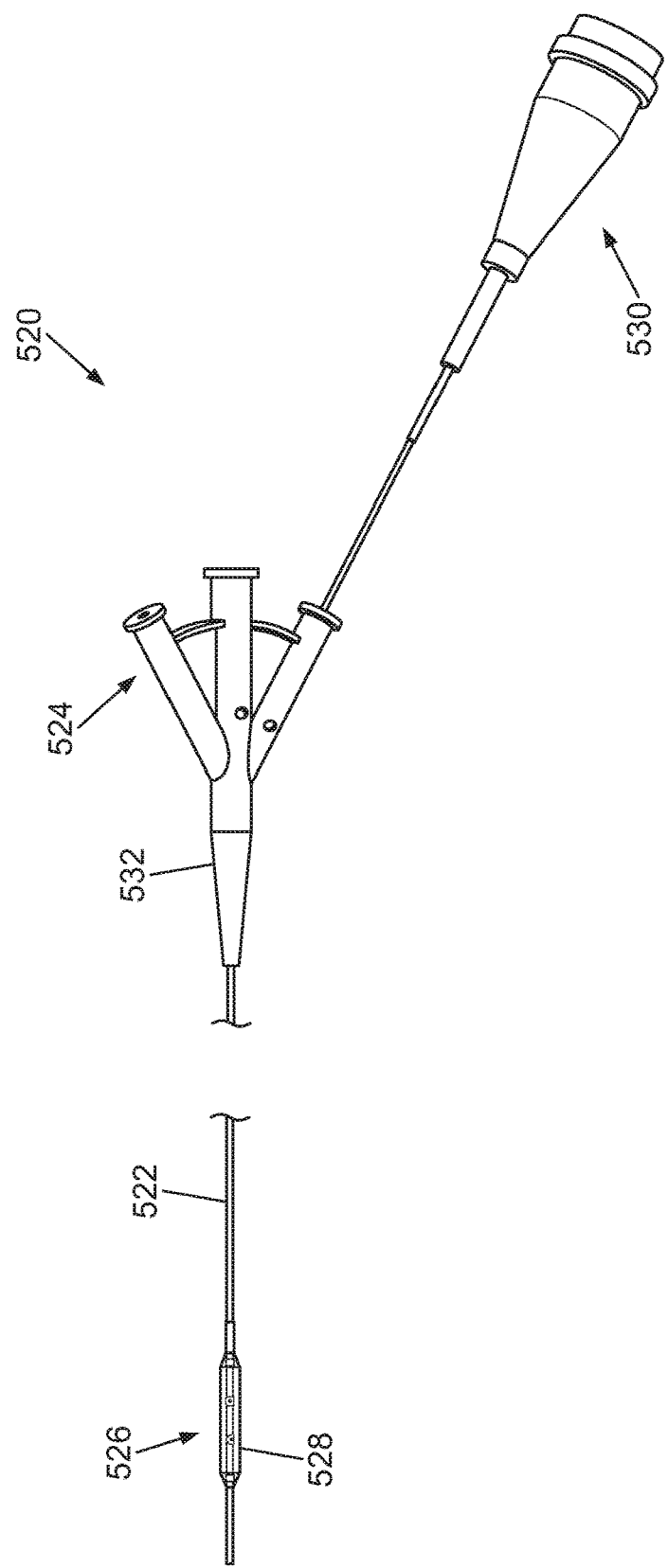
FIG. 5A depicts another variation of a shockwave angioplasty device.
Figure 5B:
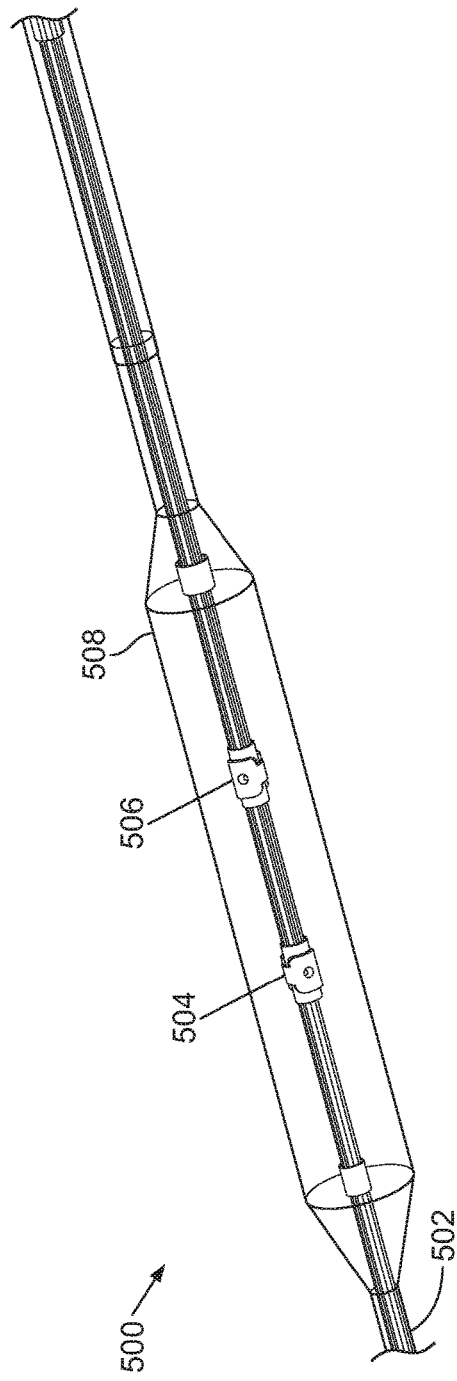
FIGS. 5B and 5C are perspective views of a plurality of low-profile shockwave electrode assemblies that may be used in a shockwave angioplasty device.
Figure 5C:
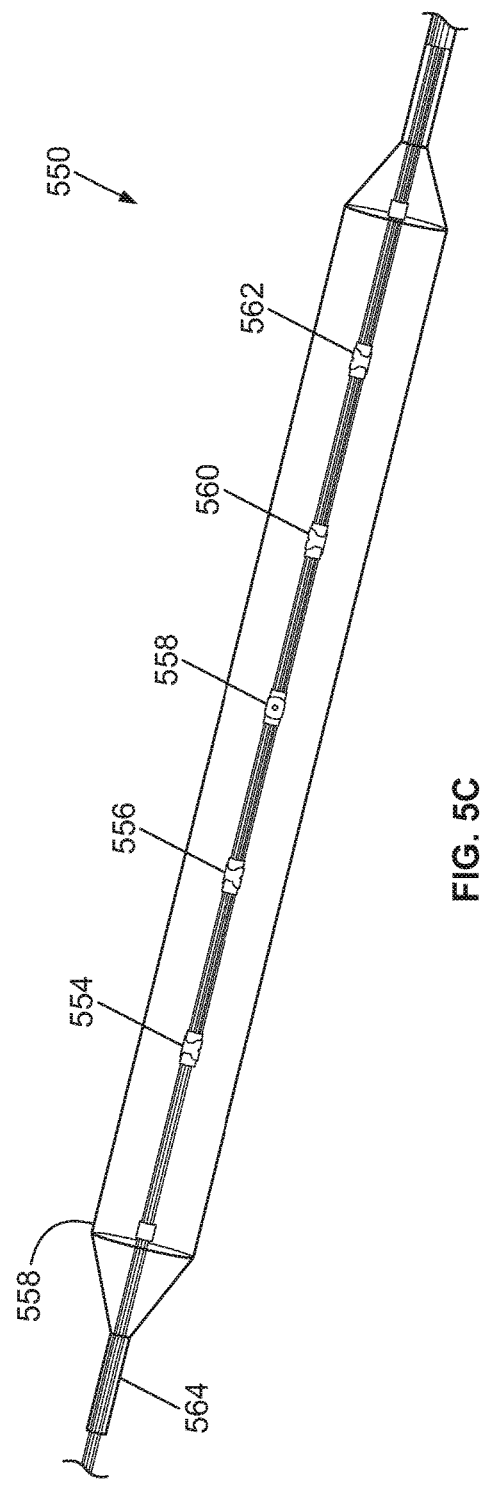

One example of a shockwave device which may be configured for shockwave angioplasty is depicted in FIG. 5A-5F. Shockwave angioplasty system 520 may comprise a catheter 522, a proximal hub 524, one or more shockwave electrode assemblies 526 at a distal portion of the catheter, a high-voltage connector 530 for connecting the shockwave assemblies to a pulse generator, and an angioplasty balloon 528 configured to be inflated with a fluid. A proximal portion of the wires from the shockwave assemblies may form a cable 576 that may be enclosed in a jacket. The cable may extend from a lumen of the proximal hub 524 and connect to the high-voltage connector 530. Pins within the high-voltage connector may connect each of the wires from the shockwave assemblies to the appropriate channel on a high voltage pulse generator. Optionally, the system 520 may additional comprise a strain relief tube 532 connected to the hub 524. The catheter 522 may have a guide wire lumen therethrough. There may be any number of shockwave electrode assemblies located at the distal end of the catheter and enclosed by the balloon. For example, there may be one shockwave electrode, two shockwave electrode assemblies, four shockwave electrode assemblies, five shockwave electrode assemblies or more. FIGS. 5B and 5C depict the distal portions of shockwave devices with two electrode assemblies and five electrode assemblies. FIG. 5B depicts one variation of a shockwave device 500 comprising an elongate member 502, a first electrode assembly 504 at a first location along the length of the elongate member, a second electrode assembly 506 at a second location along the length of the elongate member, and a balloon 508 configured to be filled with a fluid to sealably enclose the first and second electrode assemblies. The balloon 508 may be made of an electrically insulating material that may be rigid (e.g., PET, etc.), semi-rigid (e.g., PBAX, nylon, PEBA, polyethylene, etc.), or flexible (e.g., polyurethane, silicone, etc.). The first and second electrode assemblies may be spaced apart along the length of the elongate member, and may be from about 3 mm to about 20 mm apart from each other, e.g., about 5 mm, 7 mm, 10 mm. The length of the balloon may vary depending on the number of electrode assemblies and the spacing between each of the electrode assemblies. For example, a balloon for a shockwave device with two electrode assemblies spaced about 7 mm apart (e.g., 6.7 mm) may have a length of about 20 mm. A balloon for a shockwave device with five electrode assemblies spaced about 10 mm apart may have a length of about 60 mm. The electrode assemblies 504, 506 each comprise two inner electrodes that are positioned circumferentially opposite each other, an insulating sheath with two openings aligned over the two inner electrodes, and an outer electrode sheath with two openings that are coaxially aligned with the two openings of the insulating sheath. Each of the electrode assemblies 504, 506 are configured to generate a pair of directed shockwaves, where the shockwaves resulting from a high voltage pulse to the first inner electrode propagate in a direction that is opposite to the direction of the shockwaves resulting from a high voltage pulse to the second inner electrode. The electrode assemblies 504, 506 may generate shockwaves that propagate outward from different locations around the circumference of elongate member 502. For example, the electrode assembly 504 may generate shockwaves that propagate from the left and right longitudinal side of the elongate member, while the electrode assembly 506 may generate shockwaves that propagate from the top and bottom longitudinal side of the elongate member. In some variations, the electrode assembly 504 may generate a pair of shockwaves that propagate outward from positions at 0 degrees and 180 degrees around the circumference of the elongate member 502, while the electrode assembly 506 may generate a pair of shockwaves that propagate outward from positions at 60 degrees and 240 degrees around the circumference of the elongate member. In still other variations, electrode assemblies 504, 506 may each generate a pair of shockwaves that propagate outward at the same locations around the circumference of the elongate member, but from different locations along the length of the elongate member. Optionally, a radiopaque marker bands may be provided along the length of the elongate member to allow a practitioner to identify the location and/or orientation of the shockwave device as it is inserted through the vasculature of a patient. For example, there may be a first marker band proximal to the first electrode assembly and a second marker band distal to the second electrode assembly. In some variations, one or more marker bands may be located proximal to the proximal-most electrode assembly, and/or distal to the distal-most electrode assembly, and/or in the center of the elongate member and/or any other location along the length of the elongate member.

FIG. 5C depicts another shockwave device 550 comprising an elongate member 552, a first electrode assembly 554, a second electrode assembly 556, a third electrode assembly 558, a fourth electrode assembly 560, a fifth electrode assembly 562, and a balloon 564 configured to be filled with a fluid to sealably enclose the first, second, third, fourth, and fifth electrode assemblies. The balloon 564 may be made of an electrically insulating material that may be rigid (e.g., PET, etc.), semi-rigid (e.g., PBAX, nylon, PEBA, polyethylene, etc.), or flexible (e.g., polyurethane, silicone, etc.). The electrode assemblies of shockwave device 550 may be similar to the ones described in FIG. 5B, and/or may be similar to any of the electrodes described herein. The elongate member may be a catheter with a longitudinal guide wire lumen. Each of the electrode assemblies are configured to generate a pair of shockwaves that propagate in two opposite directions from the side of the elongate member. The electrode assemblies of FIG. 5C may be configured to generate shockwaves that propagate outward from different locations around the circumference of elongate member, as described above for FIG. 5B. Although the figures herein may depict shockwave devices with two or five electrode assemblies, it should be understood that a shockwave device may have any number of electrode assemblies, for example, 3, 4, 6, 7, 8, 9, 10, 15, 20, etc. The electrode assemblies may be spaced apart along the length of the elongate member, and may be from about 3 mm to about 10 mm apart from each other, e.g., about 5 mm, 8 mm, 10 mm, etc. depending on the number of electrode assemblies and the length of the elongate member that is enclosed within the balloon. Shockwave devices with a plurality of electrode assemblies distributed along the length of a catheter may be suitable for use in angioplasty procedures to break up calcified plaques that may be located along a length of a vessel. Shockwave devices with a plurality of electrode assemblies along the length of a curved elongate member may be suitable for use in valvuloplasty procedures to break up calcified plaques that may be located around the circumference of a valve (e.g., at or around the leaflets of a valve). The electrode assemblies of FIGS. 5A-5C may be similar to the electrode assemblies described above and depicted in FIGS. 3A-3E, and/or may be any of the electrode assemblies described below.

Figure 5D:
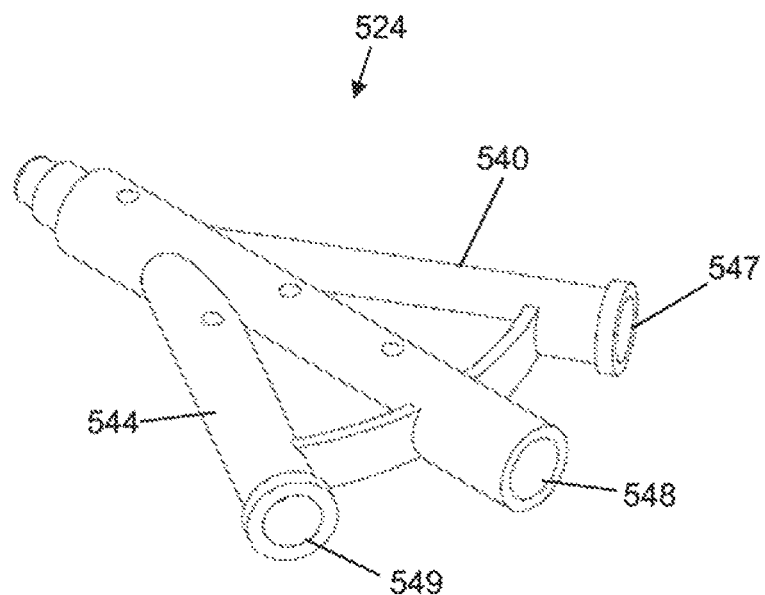
FIGS. 5D and 5E are perspective and side views of a proximal hub of a shockwave angioplasty device.
Figure 5E:
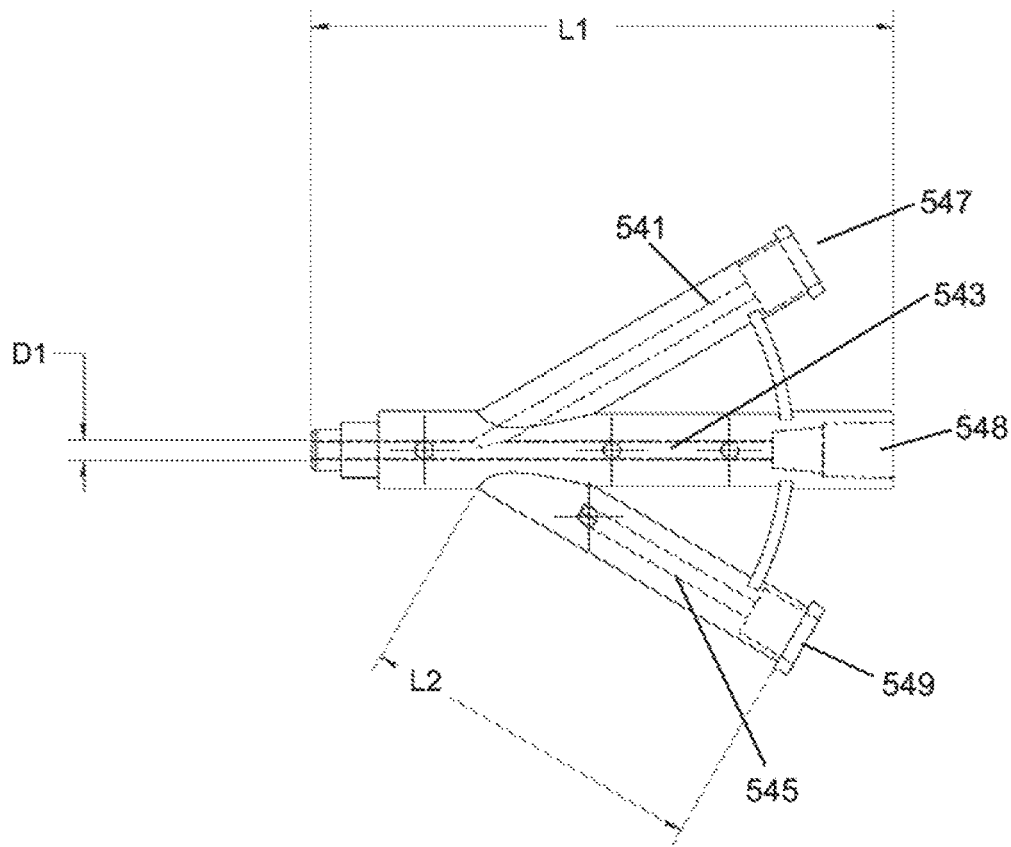

FIGS. 5D and 5E are detailed views of the proximal hub 524. As shown there, proximal hub 524 may comprise a central shaft 542, a first side shaft 540 and a second side shaft 544. The first and second side shafts are attached to either side of the central shaft 542. The central shaft 542 may have a proximal opening 548 that is connected to an inner lumen 543 that extends through the length of the central shaft and terminates at a distal opening 546 that is configured to interface with the strain relief and the catheter 522. The inner lumen 543 may be in communication and/or continuous with the guide wire lumen of the catheter 522.

The first side shaft 540 may have an opening 547 that is connected to an inner lumen 541, which is in communication and/or continuous with the inner lumen 543 of the central shaft 542. The second side shaft 544 may have an opening 549 that is connected to an inner lumen 545. The inner lumen 545 of the second side shaft 544 may not be connected to the central inner lumen 543. The inner lumens 541, 543, 545 may each have a wider proximal region and a narrower distal region, which may act as a stop for the devices inserted into the shafts. The central shaft 548 and its inner lumen 543 may function as a port for the insertion of a guidewire and/or to deliver an imaging contrast agent to the distal end of the catheter 522. The first side shaft 540 and inner lumen 541 may function as an inflation port for saline and/or imaging contrast agent. The second side shaft 549 and inner lumen 545 may function as a port through which the cable 576 may extend and connect to the high voltage connector 530 to electrically connect a high voltage pulse generator to the shockwave electrode assemblies at the distal end of the catheter. The cable 576 may be bonded to the connector 530 and/or the hub. In some variations, the proximal hub 524 may be made of injection molded polycarbonate. The length L1 of the central shaft 542 may be from about 2 inches to about 4 inches, e.g., about 2.3 inches or 2.317 inches, while the length L2 of the side shafts 540, 544 may be from about 1 inch to about 2 inches, e.g., about 1.4 inches or 1.378 inches. The diameter D1 of the narrowest portion of the central inner lumen D1 may be from about 0.05 inch to about 0.1 inch, e.g., about 0.08 inch to about 0.082 inch.

Figure 5F:
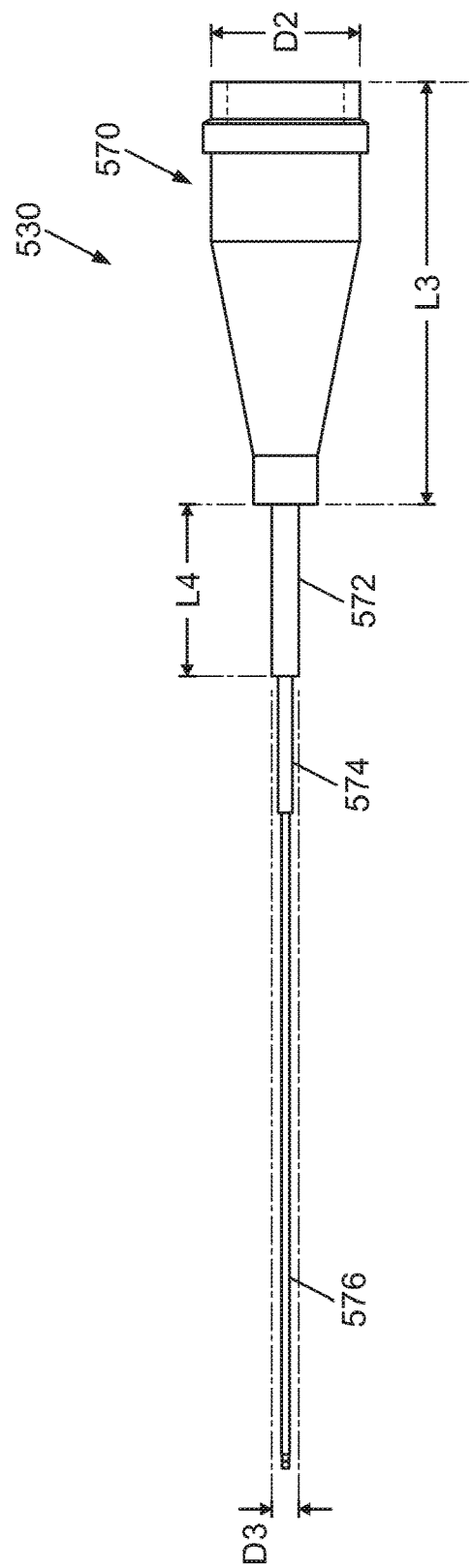
FIG. 5F is a side view of a high-voltage connector of a shockwave angioplasty device.

FIG. 5F is a detailed view of the high voltage connector 530 that may be inserted through at least one of the ports of the proximal hub, and configured to connect the shockwave electrode assemblies 526 to a high voltage pulse generator. The high voltage connector 530 may have a proximal port 570 that is configured to connect with a port of a high voltage pulse generator, a first shaft region 572, and a second shaft region 574 that is narrower than the first shaft region 572 that may connect to cable 576. The first shaft region 572 may have a diameter D3 that is greater than the diameter of the narrower portion of an inner lumen of the proximal hub, but smaller than the diameter of the wider portion of the inner lumen. The second shaft region 574 distal to the first shaft region may be configured for strain relief. For example, the cable 576 may provide connections for both the high voltage pulse(s) and the return path between the voltage pulse generator and the electrode assemblies. In some variations, the cable may provide one or more high voltage supply connections to the electrode assemblies, with one or more return connections. For example, the cable may provide for a single high voltage supply connection and a single return connection to the electrode assemblies. Alternatively, the cable may provide for a plurality of high voltage supply connections (e.g., four) and one or more return connections to the electrode assemblies. The proximal port 570 may have a length L3 from about 1.5 inches to about 3 inches, e.g., about 2 inches or 2.059 inches, and a diameter D2 from about 0.2 inch to about 1 inch, e.g., about 0.7 inch or 0.72 inch. The diameter D3 of the first shaft region 572 may be from about 0.05 in to about 0.2 inch, e.g., about 0.1 inch or 0.112 inch.

Figure 6A:
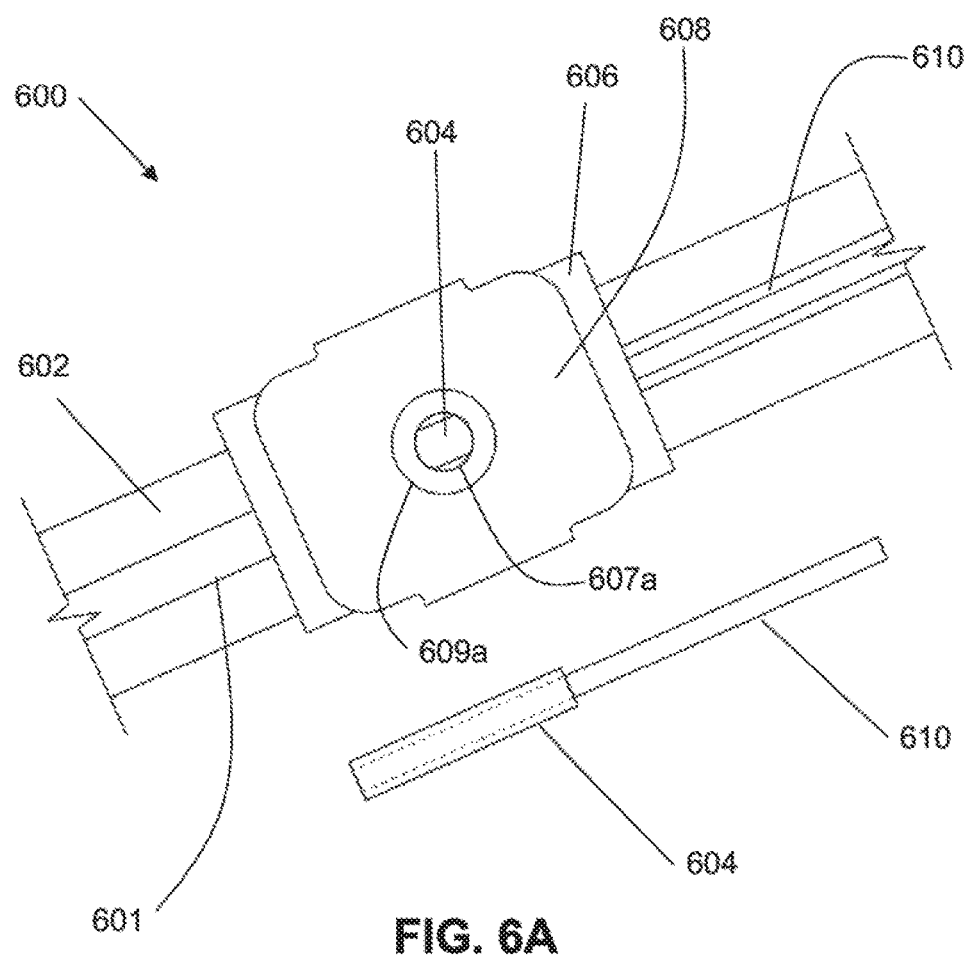
FIG. 6A depicts a top view of one variation of a low-profile shockwave electrode assembly and one variation of an inner electrode.

FIG. 6A depicts another variation of a low-profile coaxial shockwave electrode assembly that may be used in any of the shockwave devices described herein. The electrode assembly 600 may comprise a first inner electrode 604, an insulating layer or sheath 606 disposed over the first inner electrode and circumferentially wrapped around an elongate member 602 (e.g., a catheter with a guidewire lumen), and an outer electrode sheath 608 disposed over the insulating sheath. While the insulating sheath is depicted as fully circumscribing the elongate member, it should be understood that in other variations, an insulating layer may not fully circumscribe the elongate member, and may instead be disposed over certain portions of the elongate member. The insulating sheath 606 may have a first opening 607a that is coaxially aligned over the first inner electrode 604, and the outer electrode sheath 608 may have a first opening 609a that is coaxially aligned over the first opening of the insulating sheath. The electrode assembly 600 may also comprise a second inner electrode that is circumferentially opposite (or otherwise displaced from) the first inner electrode (and therefore not depicted in the view shown in FIG. 6A). The insulating sheath may have a second opening 607b that is coaxially aligned over the second inner electrode, and the outer electrode sheath may have a second opening 609b that is coaxially aligned over the second opening of the insulating sheath. The first inner electrode coaxial with the first openings in the insulating sheath and the outer electrode sheath may generate a first shockwave that propagates outwards in a first direction and the second inner electrode coaxial with the second openings in the insulating sheath and the outer electrode sheath may generate a second shockwave that propagates outwards in a second direction that is opposite to the first direction. The diameter of the openings in the outer electrode sheath may be larger than the diameter of the openings in the insulating sheath. The size of and ratio between the diameter of the openings in the outer electrode and the openings in the insulating sheath may be adjusted to attain the desired shockwave characteristics, as described above. The edges of the openings in any of the outer electrodes described herein may be electropolished. Alternatively, some variations of an electrode assembly may not have an insulating sheath or layer disposed over the elongate member, but may instead comprise an inner electrode having an insulating coating directly applied over the inner electrode (e.g., disposed over the crimped hypotube of the inner electrode). The insulating coating may cover the inner electrode such that a region of the conductive portion of the inner electrode is exposed, while the rest of the inner electrode is covered by the coating. The opening in the outer electrode sheath may be coaxially aligned with the exposed region of the inner electrode. The thickness and/or material of the insulating coating may be varied depending on the magnitude of the voltage to be applied on the electrode. Examples of insulating coatings may be Teflon, polyimide, etc. Using an insulating coating on the inner electrode instead of an insulating layer disposed over the elongate body may further reduce the crossing profile of the electrode assembly, and may allow for more bending or a tighter turning radius than an electrode assembly having an insulating sheath.

The inner electrodes and the outer electrode may each be connected to a high voltage pulse generator via a plurality of wires 610 that may be located within a plurality of longitudinal grooves 601 along the outer surface of the elongate member 602 (e.g., a catheter having a guidewire lumen) of the shockwave device. The wires may be electrically insulated along its length (e.g., by an insulating coating or sheath made of, for example, polyimide, PEBA, PET, FEP, PTFE, etc.) except for one or more regions where the electrically conductive core of the wire is exposed to contact a portion of the inner and/or outer electrode. For example, the insulating coating or sheath at the distal tip of the wire may be stripped to expose the conductive portion. The wires may be made of any conductive material, for example, free oxygen copper or copper or silver. The inner electrode 604 may be a hypotube that is crimped over the distal tip of the wire 610, where the wire 610 is enclosed within one of a plurality of grooves 601 of the elongate member. The hypotube may be made of stainless steel, tungsten, a platinum-iridium alloy, or any other material with similar hardness. In variations of an electrode assembly without an insulating layer disposed over the elongate member, a portion of the hypotube may be coated with an insulating material as described above. Each groove of the elongate member may partially enclose a single wire. For example, the wire 610 may be half enclosed within a groove of the elongate member, such that half of the wire is recessed or embedded within the groove and half of the wire protrudes outside of the groove. The wire 610 may be slidably disposed within the groove. As the elongate member is curved or bent (e.g., during an angioplasty procedure where the elongate member is a catheter that is advanced through a patient's vasculature), the wire may slide within the groove to accommodate changes in the radius of curvature as the elongate member bends, thereby minimally interfering with the flexibility of the elongate member. Optionally, one or more shrink tubes may be provided to retain the wire within the groove without impinging on its ability to move and shift as the elongate member bends or curves. For example, one or more bands of shrink tubes may be located circumferentially around the distal portion of the elongate member. Alternatively or additionally or optionally, dots of epoxy may be applied along a distal length of the wires to partially secure or retain the wires within the grooves while still maintaining the ability of the wires to partially move and shift as the elongate member bends or curves. In some variations, the wires may slide within the grooves without any retaining elements. Additional details regarding the longitudinal grooves of the elongate member are provided below.

Figure 6B:
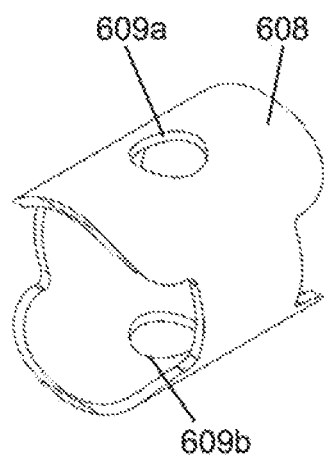
FIGS. 6B and 6C depict various views of one variation of an outer electrode sheath of a shockwave electrode assembly.
Figure 6C:
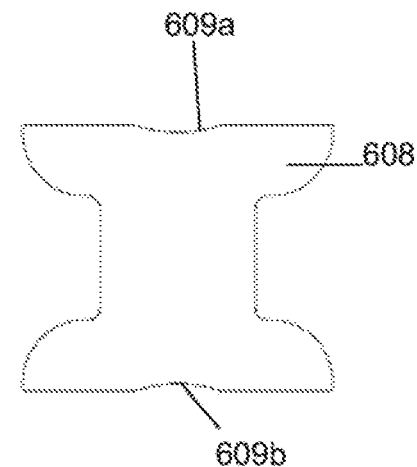
Figure 6D:
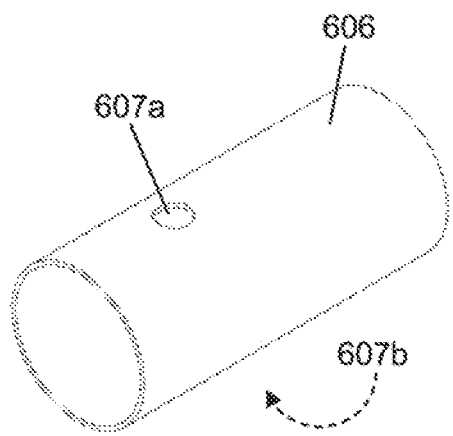
FIG. 6D depicts one variation of an insulating sheath of a shockwave electrode assembly.
Figure 6E:
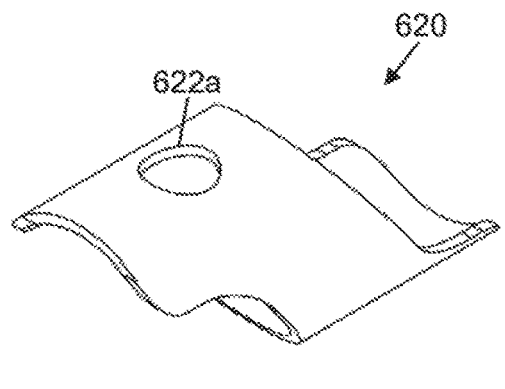
FIGS. 6E-6G depict other variations of an outer electrode sheath and insulating sheath.
Figure 6F:
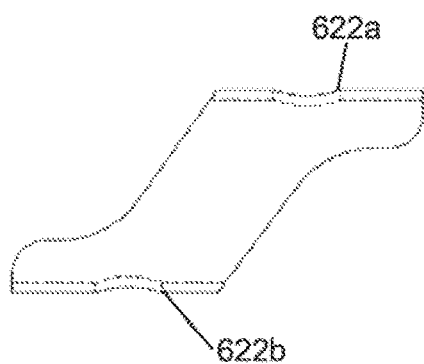
Figure 6G:
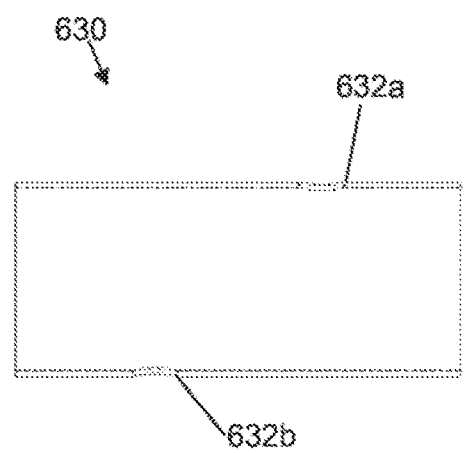

FIGS. 6B and 6C depict perspective and side view of the outer electrode sheath 608. In some variations, the outer electrode may be a radiopaque marker band (e.g., marker band used in angioplasty procedures). As depicted there, the first opening 609a may be located directly across from the second opening 609b. FIG. 6D depicts a perspective view of the insulating sheath 606 having a first opening 607a and a second opening 607b located directed across from the first opening 607a. As described above, each of these openings may be coaxially aligned with the openings of the insulating sheath 606 and first and second inner electrodes to form two shockwave sources capable of generating two shockwaves that propagate outward from the side of the elongate member in two opposite directions. FIGS. 6E and 6F depict another variation of an outer electrode sheath 620 that comprises two openings 622a, 622b that are circumferentially across each other, but laterally offset. The diameter of each of the openings 622a, 622b may be from about 0.010 inch to about 0.024 inch, e.g., about 0.014 inch. FIG. 6G depicts a variation of an insulating sheath 630 that comprises two openings 632a, 632b that are circumferentially across each other, but laterally offset. The diameter of each of the openings 632a, 632b may be from about 0.004 inch to about 0.01 inch, e.g., about 0.008 inch. The size and ratio of the openings in the insulating sheath and the outer electrode may be similar to those described previously (see FIG. 2 and accompanying description). The openings 622a, 622b of the outer electrode sheath may be coaxially aligned with the openings 632a, 632b of the insulating sheath 630, respectively. The outer electrode sheath 620 and the insulating sheath 630 may be used with a pair of inner electrodes that are similarly circumferentially across each other, but laterally offset such that the two inner electrodes are each coaxially aligned with the each of the openings in the insulating sheath and the outer electrode sheath. This may functionally create two shockwave sources configured to generate two shockwaves that propagate outward in two directions that are opposite each other but laterally offset.

Figure 6H:
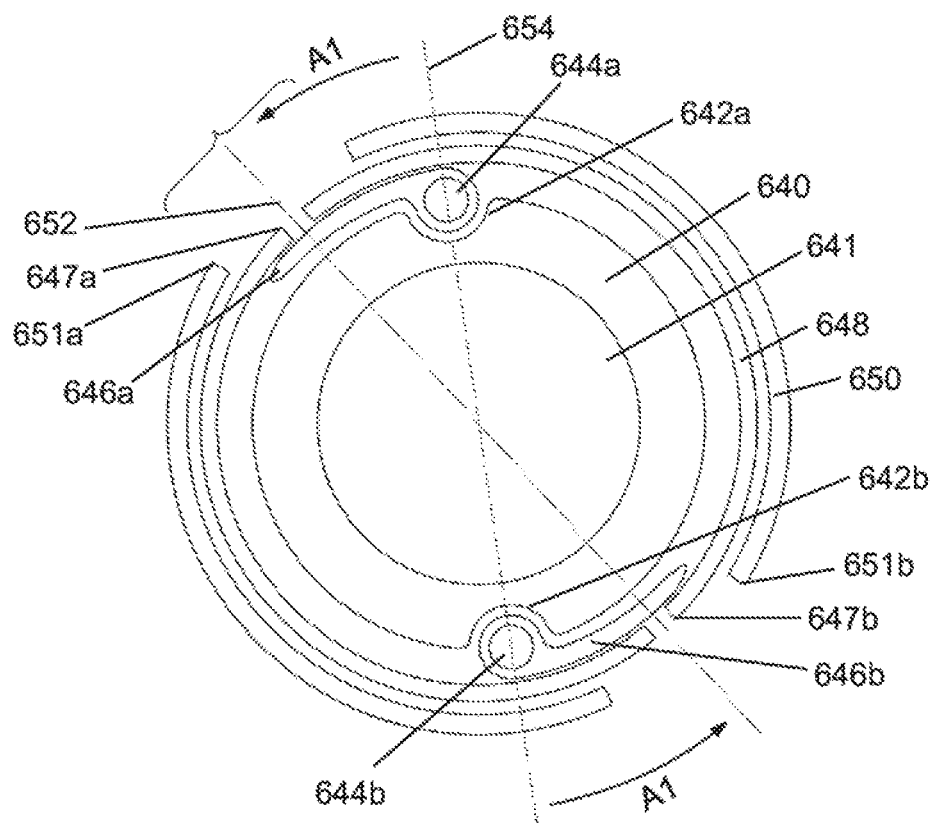
FIG. 6H depicts another variation of an inner electrode of a shockwave electrode assembly.

In the variations of the shockwave electrode assemblies described above, the inner electrode is retained within a longitudinal groove of a catheter, and the openings of an insulating sheath and outer electrode are coaxially aligned with the inner electrode. As a result, the circumferential position of the openings in the insulating sheath and the outer electrode (and therefore, the circumferential position of a shockwave source) may be constrained by the circumferential position of the longitudinal groove that retains the inner electrode. In some variations, it may be desirable to position a shockwave source at a circumferential position around the elongate member that is different from the circumferential position of the groove that retains the inner electrode. That is, the location of the shockwave source as defined by the circumferential location of the openings in the insulating sheath and outer electrode sheath may be offset with respect to the groove. A cross-section of such shockwave electrode assembly is depicted in FIG. 6H. Depicted there is a catheter 640 with a central guide wire lumen 641 and first and second grooves 642a, 642b that are located circumferentially opposite each other (e.g., 180 degrees around the catheter). First and second wires 644a, 644b are retained within the grooves 642a, 642b and are connected to first and second inner electrodes 646a, 646b. The first and section wire 644a, 644b and grooves 642a, 642b are aligned along axis 654. However, it may be desirable to have a shockwave source be located at a location that is offset from a first axis 654, for example at a location that is radially offset by angle A1 (which may be from about 1 degree to about 179 degrees). To form a shockwave electrode assembly that is offset by angle A1 from the first axis 654, the first and second inner electrodes 646a, 646b may each be a hypotube that is asymmetrically crimped so that a length of the hypotube circumferentially spans a portion of the catheter. For example, in the variation shown in FIG. 6H, the inner electrodes 646a, 646b may span at least an angle A1 along the circumference of the catheter 640. The first and second openings 647a, 647b of the insulating sheath 648 may be coaxially aligned over the first and second inner electrodes at the radially offset location, and the first and second openings 651a, 651b of the outer electrode 650 may be coaxially aligned over first and second openings 647a, 647b of the insulating sheath 648. In other words, the first and second openings 647a, 647b of the insulating sheath 648, the first and second openings 651a, 651b of the outer electrode 650, and a portion of the first and second inner electrodes 646a, 646b may be coaxially aligned along a second axis 652 that is offset by angle A1 from the first axis 654. Such configuration may allow for the placement of a shockwave source anywhere along the circumference of a catheter without necessarily being aligned with the circumferential location of the one more longitudinal grooves of the catheter.

Figure 7A:
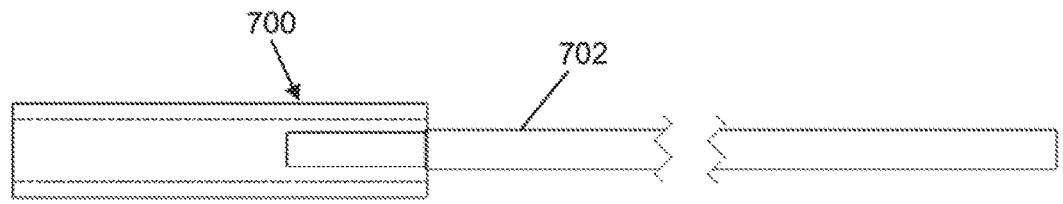
FIGS. 7A-7D depict one method of assembling a low-profile shockwave electrode assembly.
Figure 7B:
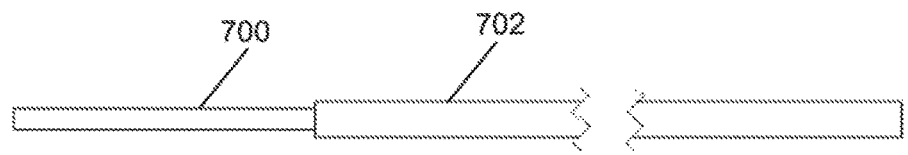
Figure 7C:
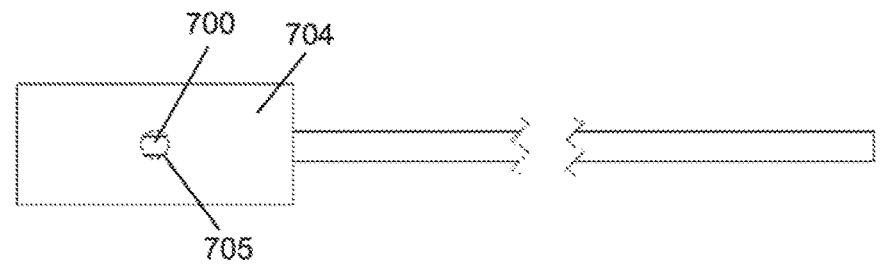
Figure 7D:
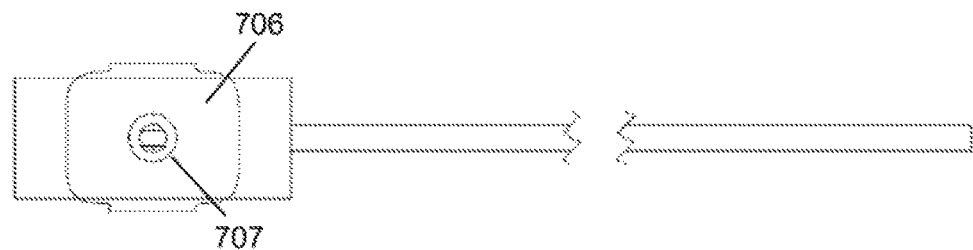

The low-profile shockwave electrode assembly depicted in FIG. 6A may be assembled in any suitable fashion. FIGS. 7A-7D depict an example of a method for making a low-profile shockwave electrode assembly that is located along a length of an elongate member (which for clarity purposes, is not shown here). The inner electrode 700 may be a hypotube that is placed over an exposed core of a wire 702 and crimped and flattened, as illustrated in FIGS. 7A and 7B. In some variations, the inner electrode 700 may be crimped and flattened with a slight curve to approximate and/or match the radius of curvature of the elongate member. The inner electrode 700 and the wire 702 are then placed within a longitudinal groove of the elongate member (see FIG. 6A). An insulating layer or sheath 704 may be slid over the elongate member and positioned over the inner electrode 700 such that an opening 705 of the insulating sheath 704 is coaxially aligned over the inner electrode, as shown in FIG. 7C. An outer electrode sheath 706 may be slid over the elongate member and positioned over the insulating sheath 704 such that an opening 707 of the outer electrode sheath 706 is coaxially aligned over the opening 705 of the insulating sheath 704, as shown in FIG. 7D. In variations of shockwave electrode assemblies that comprise a second inner electrode circumferentially opposite to the first inner electrode 700, aligning the openings of the insulating sheath and the outer electrode over the first inner electrode may also align a second set of openings of the insulating sheath and the outer electrode over the second inner electrode. Once the outer electrode sheath and the insulating sheath have been positioned in the desired location, their location may be secured by applying a UV curable adhesive, such as Loctite 349, at both ends of the sheaths.

Figure 8A:
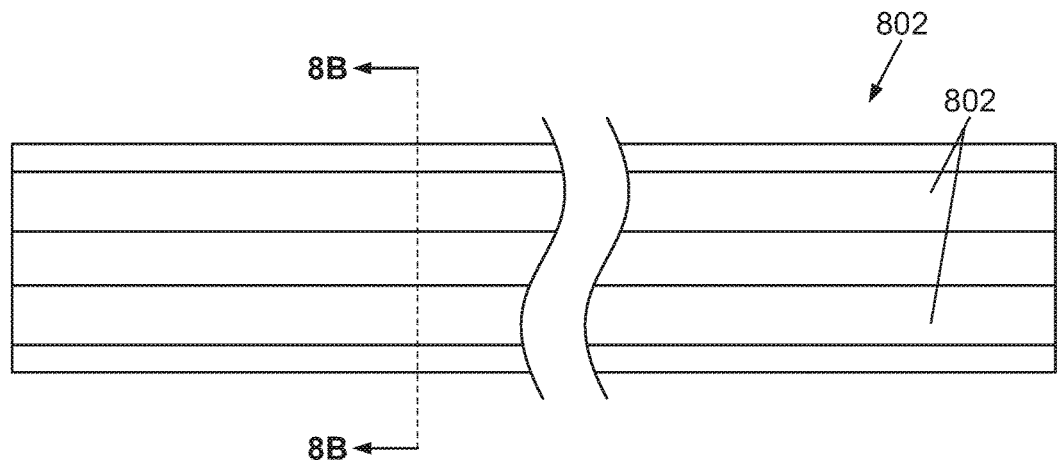
FIG. 8A depicts a side view of a catheter of a shockwave device.
Figure 8B:
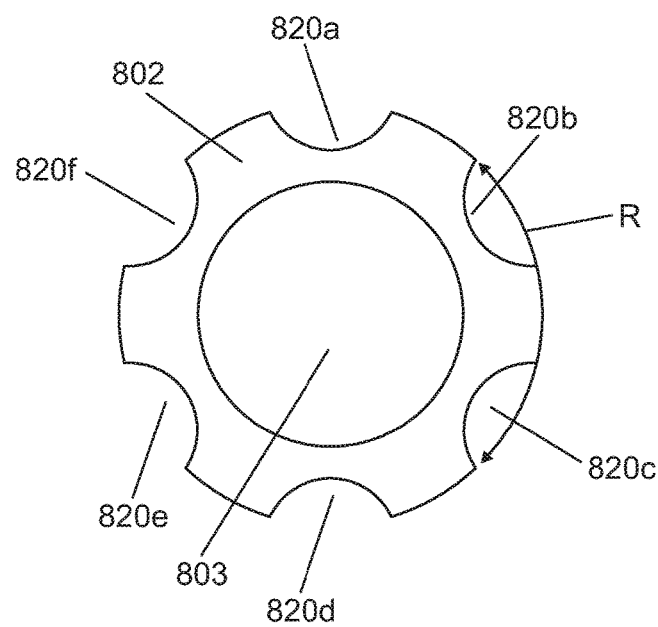
FIG. 8B is a cross-sectional view of the catheter of FIG. 8A.

FIGS. 8A and 8B depict side and cross-sectional view (taken along line 8B-8B) of one variation of a grooved elongate member (e.g., a catheter) that may be used in any of the shockwave devices described herein. The elongate member 802 may have any number of longitudinal grooves or channels configured for retaining a wire and/or inner electrode, and may for instance have 1, 2, 3, 4, 5, 6, 7, 8, 10, etc. grooves. As illustrated in FIG. 6B, the elongate member 602 has six grooves that surround a central guide wire lumen 603. In some variations, the elongate member 802 may have a radius of about 0.014 inch and the each of the grooves may have a radius of curvature of about 0.005 inch to about 0.010 inch. Where the grooves may have a semi-elliptical shape, the minor axis may be about 0.008 inch and the minor axis may be about 0.015 inch. The elongate member 802 may also comprise a guide wire lumen 803, where the guide wire lumen may have a radius of about 0.0075 inch to about 0.018 inch, e.g., about 0.02 inch or 0.0175 inch.

Optionally, shrink tubing may be provided over each of the wires to help retain the wire within the groove while still allowing the wires to slide and move within the grooves to accommodate bending of the elongate member 602. Wires slidably disposed within longitudinal grooves on the outer surface of the elongate member may retain the flexibility of the elongate member such that the elongate member may easily navigate and access tortuous vasculature. While the variations here depict wires that are slidably disposed within grooves of the elongate member to accommodate bending of the elongate member, in other variations, the wires may be conductive elements that are co-extruded with the elongate member and therefore unable to slide with respect to the elongate member. However, co-extruding conductive elements with the elongate member may stiffen the elongate member, thereby limiting its flexibility and ability to navigate to and access tortuous vasculature. For example, the smallest radius of curvature attainable by an elongate member with co-extruded conductive elements may be larger than the smallest radius of curvature attainable by an elongate member with wires slidably disposed in grooves along its outer surface. The turning radius of an elongate member that has wires slidably disposed within longitudinal grooves along its outer surface may be tighter than the turning radius of the same elongate member if the wires were unable to slide with respect to the elongate member.

Figure 9:
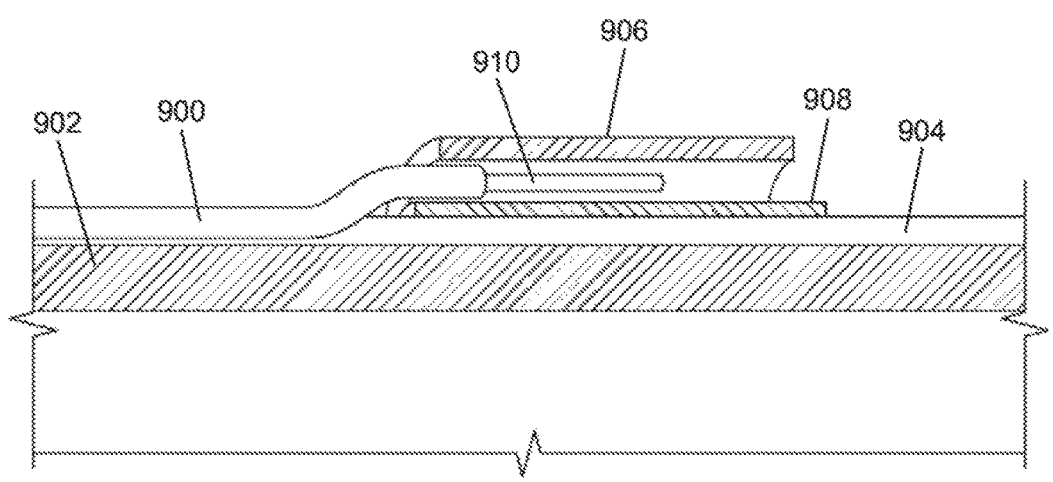
FIG. 9 is a cross-sectional view depicting the connectivity between a grooved wire and an outer electrode sheath of a shockwave electrode assembly.

The wires retained within the longitudinal grooves of an elongate member may be connected to inner electrodes, as described above, and/or may be connected to outer electrode sheaths. A wire that is retained within a longitudinal groove may be connected to an outer electrode sheath using any suitable method, for example, by friction fit and/or adhesives. For example, the wire may be friction fit between the outer electrode sheath and the insulating sheath, and optionally further secured in contact with the outer electrode sheath with an adhesive, as depicted in FIG. 9. As depicted there, a wire 900 retained within a groove 904 of an elongate member 902 may contact an outer electrode sheath 906 via a stripped portion 910 that is drawn out of the groove 904 and inserted between the outer electrode sheath and insulating sheath 908 (for clarity, the inner electrode of this this shockwave electrode assembly is not shown). The wire may be secured between the outer electrode sheath and the insulating sheath friction fit and may optionally be further secured and electrically insulated by an adhesive, such as conductive epoxy or laser welded or spot welded. Inserting the stripped portion 910 (where the electrically conductive portion is exposed) between the outer electrode sheath and the insulating sheath and further sealing it with an adhesive may help to ensure that the wire does not inadvertently contact an inner electrode or any other conductive medium (e.g., the fluid that may be used to fill a shockwave angioplasty balloon). Various connections between the wires and the inner and outer electrodes of the electrode assemblies are further described below.

The first and second inner electrodes of an electrode assembly may be connected such that they are each independently voltage-controlled, e.g., each directly connect to separate positive channels of a high voltage pulse generator. They may be independently controlled (e.g., capable of being pulsed separately) or may be controlled together. An example of direct connectivity between the first and second inner electrodes of a shockwave electrode assembly 1000 is depicted in FIGS. 10A-10D. The shockwave electrode assembly 1000 may be any of the electrode assemblies described herein, and may comprise a first inner electrode 1002, a second inner electrode 1004 and an outer electrode 1006. As schematically depicted in FIG. 7A, a first wire 1003 may connect the first inner electrode 1002 to a first voltage output port VO1 of a pulse generator 1001. A second wire 1005 may connect the second inner electrode 1004 to a second voltage output port VO2 of the pulse generator 1001. A third wire 1006 may connect the outer electrode to a third voltage output port VO3 (a ground channel or negative terminal). In some variations, the first voltage output port VO1 and the second voltage output port VO2 may be positive channels while the third voltage output port VO3 may be a negative channel (or vice versa). During a high voltage pulse on the first and/or second voltage output ports VO1, VO2, current may flow in the direction of the arrows in the first and/or second wires 1003, 1005 from the voltage outputs VO1, VO2 to the first and second inner electrodes 1002, 1004. The high voltage pulse generator may apply a voltage pulse on output port VO1 such that the potential difference between the first inner electrode 1002 and the outer electrode 1006 is high enough to form a plasma arc between them, generating a bubble that gives rise to a shockwave. Similarly, the high voltage pulse generator may simultaneously or sequentially apply a voltage pulse on output port VO2 such that the potential difference between the second inner electrode 1004 and the outer electrode 1006 is high enough to form a plasma arc between them, generating a bubble that gives rise to a different shockwave. In a variation where the first inner electrode and second inner electrode are located circumferentially opposite to each other (e.g., 180 degrees apart from each other around the circumference of the elongate member), the shockwaves generated by the first and second inner electrodes may propagate in opposite directions, extending outward from the side of the elongate member. The current that traverses the bubble from the inner electrode 1002 and/or inner electrode 1004 to the outer electrode 1006 returns via wire 1007 to voltage output port VO3 (which may be a negative channel or a ground channel). Voltage output ports VO1 and VO2 may be independently addressed (e.g., voltage and current may be applied to one output but not necessarily the other), or may be not be independently addressed (e.g., activating one output necessarily activates the other). Optionally, a connector (not shown) may be provided between the wires 1003, 1005, 1007 and the voltage pulse generator 1001 so that the wires of the elongate member may be easily connected to the output ports of the high voltage generator.

Figure 10A:
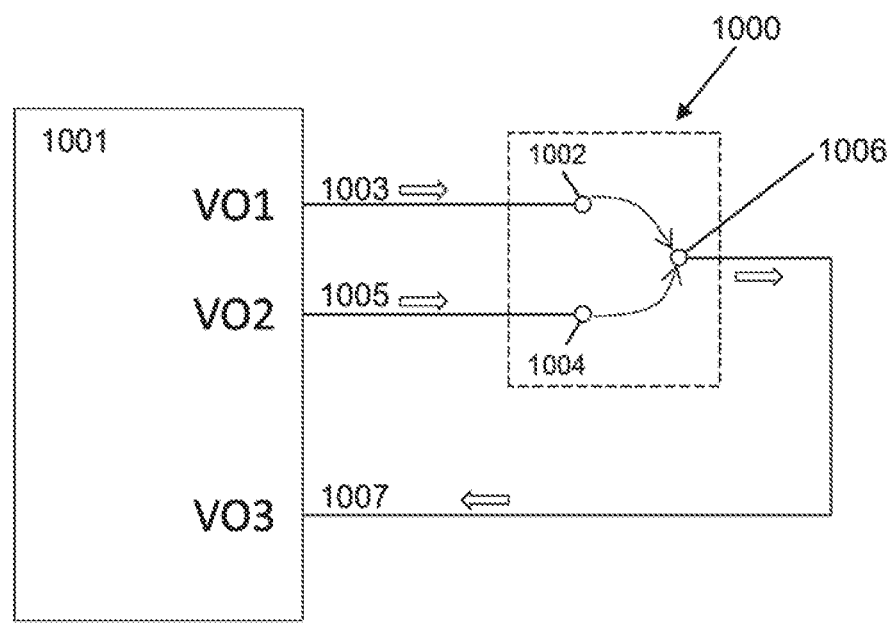
FIG. 10A schematically depicts a shockwave electrode assembly having two inner electrodes that are in a direct connect configuration.
Figure 10B:
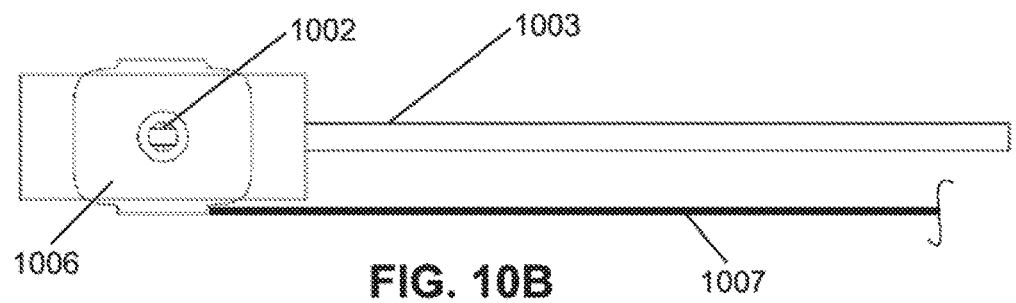
FIGS. 10B-10D depict the connectivity between the inner electrodes and outer electrodes to attain the configuration of FIG. 10A.
Figure 10C:
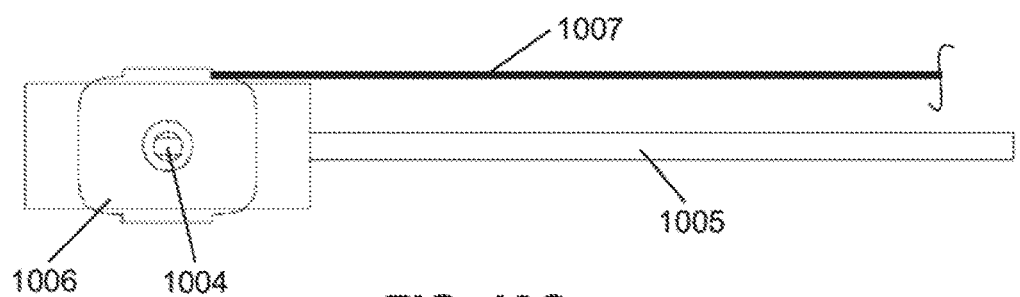
Figure 10D:
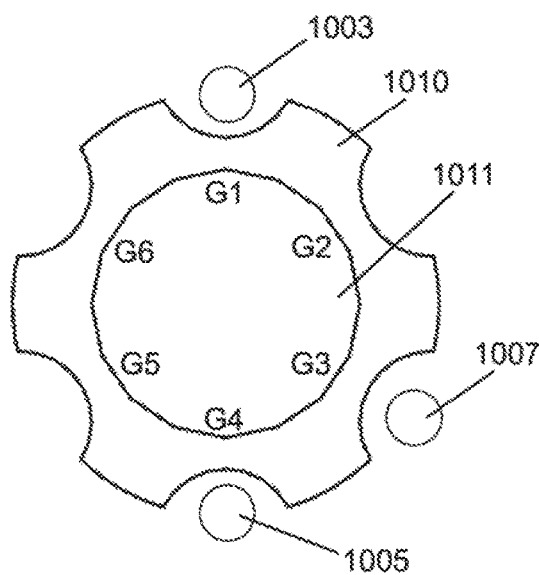

FIGS. 10B-10D depict one variation of how the circuit of FIG. 10A may be implemented in a shockwave device that comprises the shockwave electrode assembly 1000. The shockwave device may comprise a catheter 1010 with a central guide wire lumen 1011 and six longitudinal grooves (G1-G6) arranged around the guide wire lumen. FIG. 10B is a top view of the electrode assembly 1000 where the first inner electrode 1002 is visible and FIG. 10C a bottom view of the electrode assembly 1000 where the second inner electrode 1004 is visible. The first and second inner electrodes are located circumferentially opposite each other (i.e., 180 degrees apart). FIG. 10D depicts the grooves in which each of the inner electrodes and/or wires may be retained. The return wire 1007 may be connected to the outer electrode sheath 1006 in any of the configurations described above and may be retained in groove G3. The wire 1003 connects the first inner electrode 1002 with the first voltage output VO1, and may be retained in groove G1. The wire 1005 connects the second inner electrode 1004 with the second voltage output VO2, and may be retained in groove G4, directly opposite groove G1. While the example depicted here uses grooves G1, G3, and G4, it should be understood that any three of the six grooves may be used to retain the wires 1003, 1005 and 1007 to attain the connectivity depicted in FIG. 10A. For example, the wires 1003, 1005 and 1007 may be retained in grooves G2, G5 and G6 respectively, or grooves G3, G6 and G5 respectively, or grooves G1, G3, and G2 respectively, grooves G1, G3, and G5 respectively, etc.

Figure 11A:
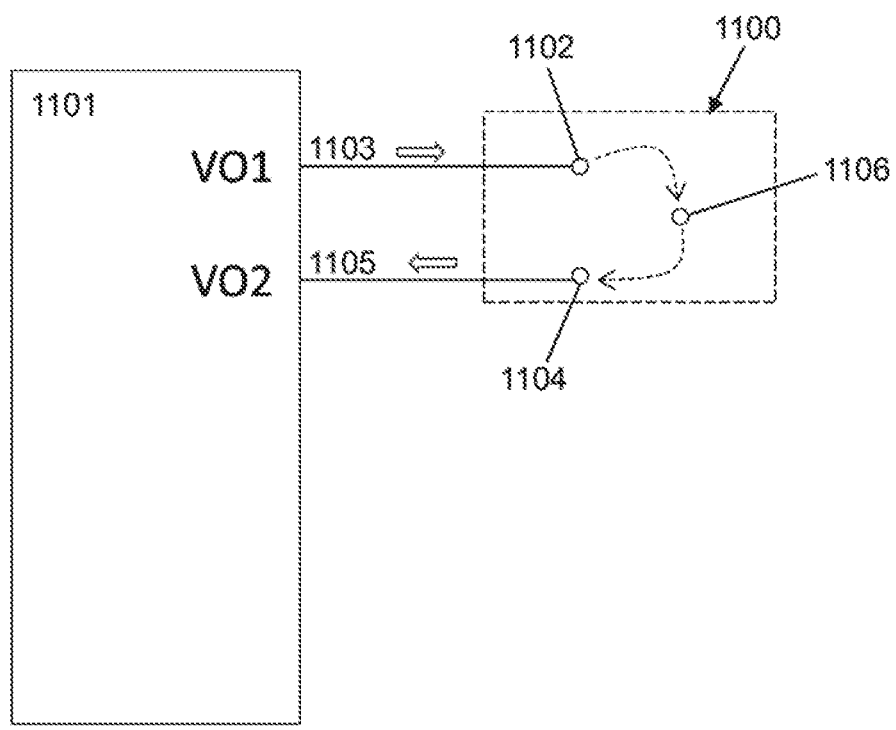
FIG. 11A schematically depicts a shockwave electrode assembly configured in series.

Alternatively, the first and second inner electrodes of an electrode assembly may be connected in series such that activating the first inner electrode also activates the second inner electrode. This may allow the electrode assembly to generate up to two shockwaves (i.e., one from each of the first and second inner electrodes) using only a single output port on the high voltage generator. FIGS. 11A-11D depict one example of a shockwave electrode assembly 1100 that is configured such that first inner electrode 1102 is in series with the second inner electrode 1104. The shockwave electrode assembly 1100 may be any of the electrode assemblies described herein, and may comprise a first inner electrode 1102, a second inner electrode 1104 and an outer electrode 1106. As schematically depicted in FIG. 11A, a first wire 1103 may connect the first inner electrode 1102 to a first voltage output port VO1 of a pulse generator 1101. A second wire 1105 may connect the second inner electrode 1104 to a second voltage output port VO2 (a ground channel or negative terminal). In some variations, the first voltage output port VO1 may be a positive channel while the second voltage output port VO2 may be a negative channel (or vice versa). During a high voltage pulse on the first voltage output port VO1, current may flow in the direction of the arrow in the first wire 1103 from the voltage output VO1 to the first inner electrode 1102. The high voltage pulse generator may apply a voltage pulse on output port VO1 such that the potential difference between the first inner electrode 1102 and the outer electrode 1106 is high enough to form a plasma arc between them, generating a bubble that gives rise to a shockwave. The current that traverses the bubble from the first inner electrode 1102 to the outer electrode 1106 may set up a potential difference between the outer electrode 1106 and the second inner electrode 1004 that is high enough to form a plasma arc between them, generating a bubble that gives rise to a different shockwave. In a variation where the first inner electrode and second inner electrode are located circumferentially opposite to each other (e.g., 180 degrees apart from each other around the circumference of the elongate member), the shockwaves generated by the first and second inner electrodes may propagate in opposite directions, extending outward from the side of the elongate member. The current then returns to the voltage source generator via wire 1105 to voltage output port VO2 (which may be a negative channel or a ground channel). Optionally, a connector (not shown) may be provided between the wires 1103, 1105 and the voltage pulse generator 1101 so that the wires of the elongate member may be easily connected to the output ports of the high voltage generator.

Figure 11B:
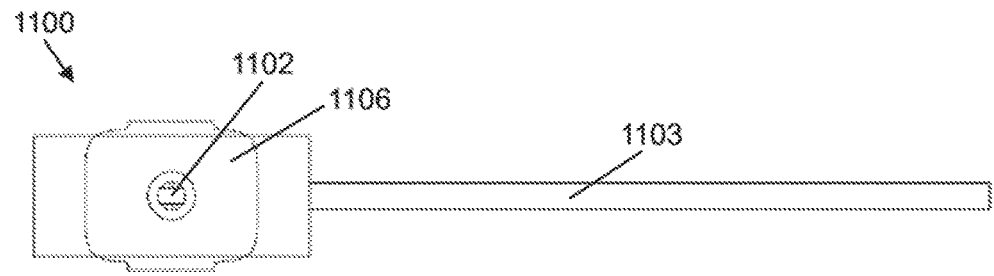
FIGS. 11B-11D depict the connectivity between the inner electrodes and outer electrodes to attain the configuration of FIG. 11A.
Figure 11C:
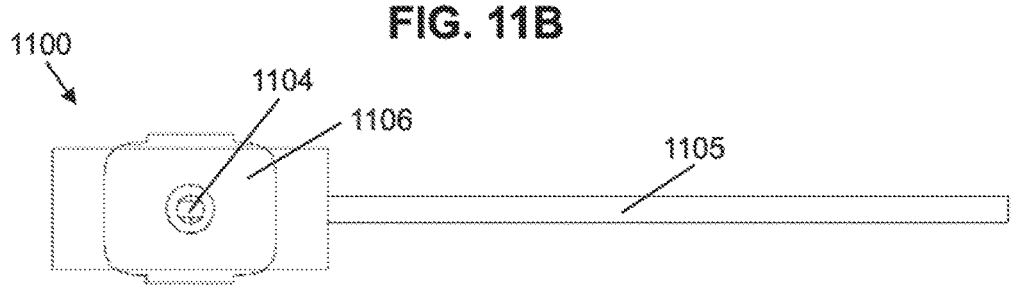
Figure 11D:
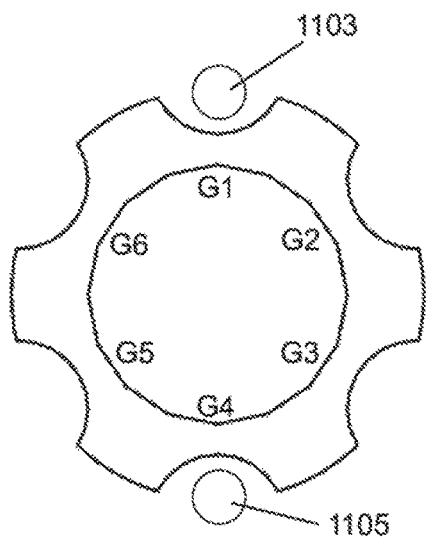

FIGS. 11B-11D depict one variation of how the circuit of FIG. 11A may be implemented in a shockwave device that comprises the shockwave electrode assembly 1100. The shockwave device may comprise a catheter 1110 with a central guide wire lumen 1111 and six longitudinal grooves (G1-G6) arranged around the guide wire lumen. FIG. 11B is a top view of the electrode assembly 1100 where the first inner electrode 1102 is visible and FIG. 11C a bottom view of the electrode assembly 1100 where the second inner electrode 1104 is visible. The first and second inner electrodes are located circumferentially opposite each other (i.e., 180 degrees apart). FIG. 11D depicts the grooves in which each of the inner electrodes and/or wires may be retained. The wire 1103 connects the first inner electrode 1102 with the first voltage output VO1, and may be retained in groove G1. The wire 1105 connects the second inner electrode 1104 with the second voltage output VO2, and may be retained in groove G4, directly opposite groove G1. While the example depicted here uses grooves G1 and G4, it should be understood that any two of the six grooves may be used to retain the wires 1103, 1105 to attain the connectivity depicted in FIG. 11A. For example, the wires 1103 and 1105 may be retained in grooves G2 and G5 respectively, or grooves G3 and G6 respectively, etc.

Some variations of shockwave devices may comprise two or more shockwave electrode assemblies. For example, the shockwave angioplasty system 520 depicted in FIG. 5A comprises two electrode assemblies where each electrode assembly has two inner electrodes circumferentially opposite to each other and is configured to generate two shockwaves that propagate outward from the side of the catheter in opposite directions. The two shockwave electrode assemblies may be connected such that each of the inner electrodes of the two electrode assemblies (i.e., for a total of four inner electrodes) are each connected to separate voltage channels.

Figure 12A:
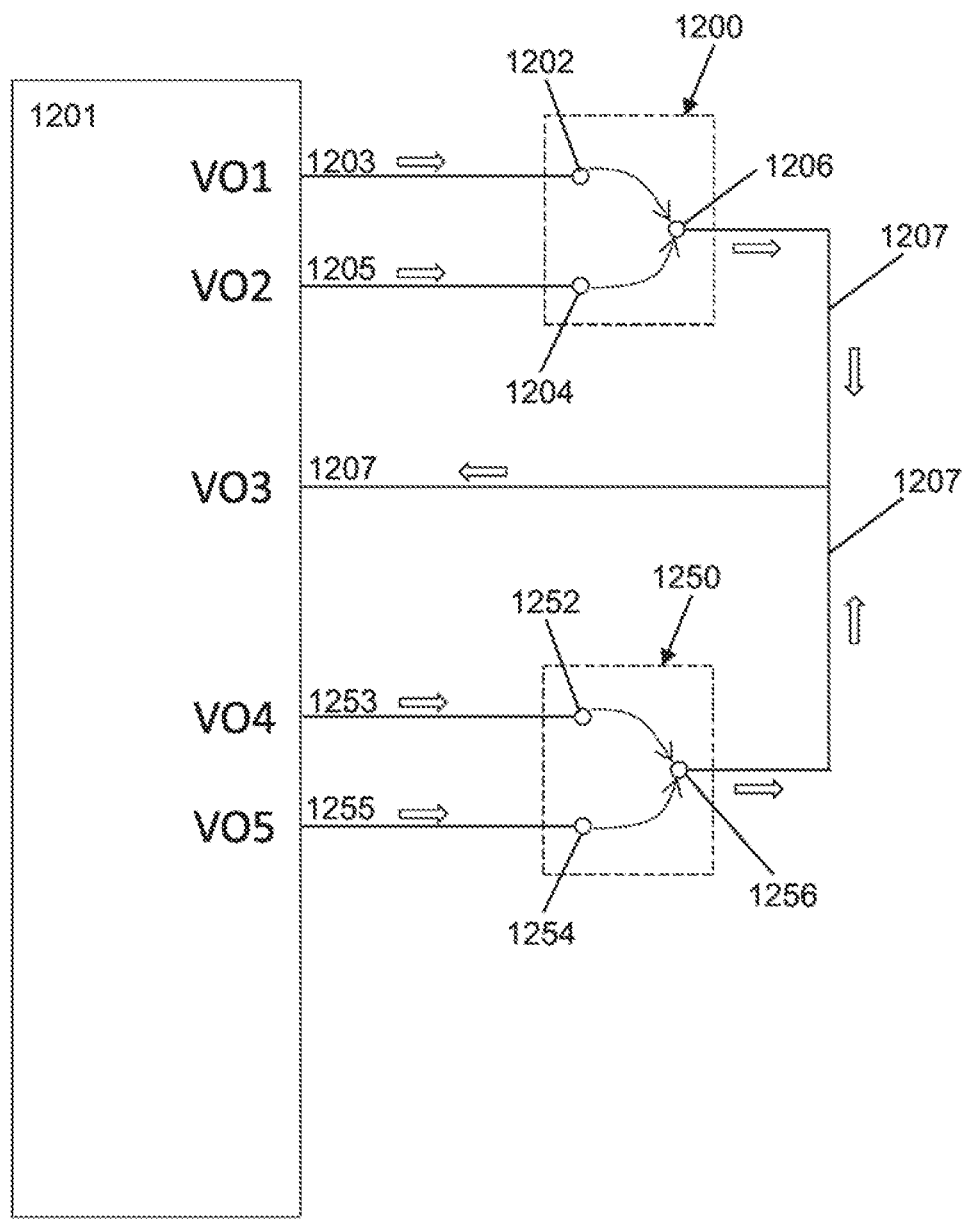
FIG. 12A schematically depicts two shockwave electrode assemblies that are in a direct connect configuration.

For example, each of the inner electrodes may each be directly connected to different voltage channels in a direct connect configuration. The inner electrodes may be individually addressable and/or can be activated by separate ports on a high voltage pulse generator. FIGS. 12A-12D depict a variations of two shockwave electrode assemblies of a shockwave device (e.g., a shockwave angioplasty device) where the first and second inner electrodes of each electrode assembly are connected such that they are each connected to separate voltage channels. The shockwave electrode assemblies 1200, 1250 may be any of the electrode assemblies described herein. The first shockwave electrode assembly 1200 may comprise a first inner electrode 1202, a second inner electrode 1204 and an outer electrode 1206. The second shockwave electrode assembly 1250 may comprise a first inner electrode 1252, a second inner electrode 1254 and an outer electrode 1256. As schematically depicted in FIG. 12A, a first wire 1203 may connect the first inner electrode 1202 of the first electrode assembly 1200 to a first voltage output port VO1 of a pulse generator 1201. A second wire 1205 may connect the second inner electrode 1204 of the first electrode assembly 1200 to a second voltage output port VO2 of the pulse generator 1201. A third wire 1207 may connect the outer electrode 1206 of the first electrode assembly to a third voltage output port VO3 (a ground channel or negative terminal). In some variations, the first voltage output port VO1 and the second voltage output port VO2 may be positive channels while the third voltage output port VO3 may be a negative channel (or vice versa). A fourth wire 1253 may connect the first inner electrode 1252 of the second electrode assembly 1250 to a fourth voltage output port VO4 of the pulse generator 1201. A fifth wire 1255 may connect the second inner electrode 1254 of the second electrode assembly 1250 to a fifth voltage output port VO5 of the pulse generator 1201. The outer electrode 1256 of the second electrode assembly may also contact the third wire 1207 and be connected to the third voltage output port VO3. In some variations, the first voltage output port VO1, the second voltage output port VO2, the fourth voltage output VO4 and the fifth voltage output VO5 may each be positive channels while the third voltage output port VO3 may be a negative channel. During a high voltage pulse on any one of the first and/or second and/or fourth and/or fifth voltage output ports VO1, VO2, VO4, VO5, current may flow in the direction of the arrows in the first and/or second and/or fourth and/or fifth wires 1203, 1205, 1253, 1255 from the voltage outputs VO1, VO2, VO4, VO5 to the first and second inner electrodes of the first and second electrode assemblies 1202, 1204, 1252, 1254 of the first and second electrode assemblies. The high voltage pulse generator may apply a voltage pulse on any one of the output ports such that the potential difference between any one of the inner electrodes and the corresponding outer electrode 1206, 1256 is high enough to form a plasma arc between them, generating a bubble that gives rise to a shockwave. Each of the plasma arcs formed between an inner electrode and an outer electrode (of the same electrode assembly) may generate a bubble that gives rise to a different shockwave. In a variation where the first inner electrode and second inner electrode are located circumferentially opposite to each other (e.g., 180 degrees apart from each other around the circumference of the elongate member), the shockwaves generated by the first and second inner electrodes may propagate in opposite directions, extending outward from the side of the elongate member. With the two electrode assemblies 1200, 1250, a total of up to four different shockwaves may be generated. The current that traverses the bubble from the inner electrodes to the corresponding outer electrode returns via wire 1207 to voltage output port VO3 (which may be a negative channel or a ground channel). In some variations, the return current from any one of the outer electrodes may be connected to an intermediate node (e.g., an optional outer electrode band or sheath, and/or optional interconnect wire) before it is connected to the wire 1207. The voltage output ports may be independently addressed or may be not be independently addressed, as previously described. Optionally, a connector (not shown) may be provided between the wires and the voltage pulse generator 1201 so that the wires of the elongate member may be easily connected to the output ports of the high voltage generator.

FIGS. 12B-12C depict one variation of how the circuit of FIG. 12A may be implemented in a shockwave device that comprises the first shockwave assembly 1200 and second shockwave electrode assembly 1250. The shockwave device may comprise a catheter 1210 with a central guide wire lumen 1211 and six longitudinal grooves (G1-G6) arranged around the guide wire lumen. FIG. 12B is a perspective view of the distal portion of the shockwave device with the first electrode assembly 1200 and second electrode assembly 1250 each at different longitudinal locations along the catheter 1210. For each electrode assembly 1200, 1250, the first and second inner electrodes are located circumferentially opposite each other (i.e., 180 degrees apart). FIG. 12C depicts the grooves in which each of the inner electrodes and/or wires may be retained, some of which are also depicted in FIG. 12B. The return wire 1207 may be connected to the outer electrode sheaths 1206, 1256 in any of the configurations described above and may be retained in groove G3. The wire 1203 connects the first inner electrode 1202 of the first electrode assembly with the first voltage output VO1, and may be retained in groove G2. The wire 1205 connects the second inner electrode 1204 of the first electrode assembly with the second voltage output VO2, and may be retained in groove G5, directly opposite groove G2. The wire 1253 connects the first inner electrode 1252 of the second electrode assembly with the fourth voltage output VO4, and may be retained in groove G1. The wire 1255 connects the second inner electrode 1254 of the second electrode assembly with the fifth voltage output VO5, and may be retained in groove G3, directly opposite groove G1. While the example depicted here uses grooves G1-G5, it should be understood that any five of the six grooves may be used to retain the wires to attain the connectivity depicted in FIG. 12A. For example, the wires 1203, 1205, 1253, 1255 and 1207 may be retained in grooves G1, G4, G2, G5, G3 respectively, or grooves G5, G3, G1, G4, G5 respectively, etc. As depicted in FIG. 12B, the circumferential locations of the inner electrodes of the first electrode assembly are different from the circumferential locations of the inner electrodes of the second electrode assembly, i.e., they are offset from each other by an angle, which angle may be any value of about 1 degree to about 179 degrees, e.g., about 60 degrees, as determined by the location of the groove in which the inner electrode is retained. However, in other variations, the inner electrode may span a circumferential length of the catheter (such as described and depicted in FIG. 6H), which may allow for the electrode assemblies to be rotated such that shockwaves may be generated from a desired circumferential location. In such variations, the orientation of the first and second electrode assemblies may be the same (i.e., shockwaves may be generated from the same circumferential location around the catheter, but longitudinally offset by the distance between the electrode assemblies).

Figure 13A:
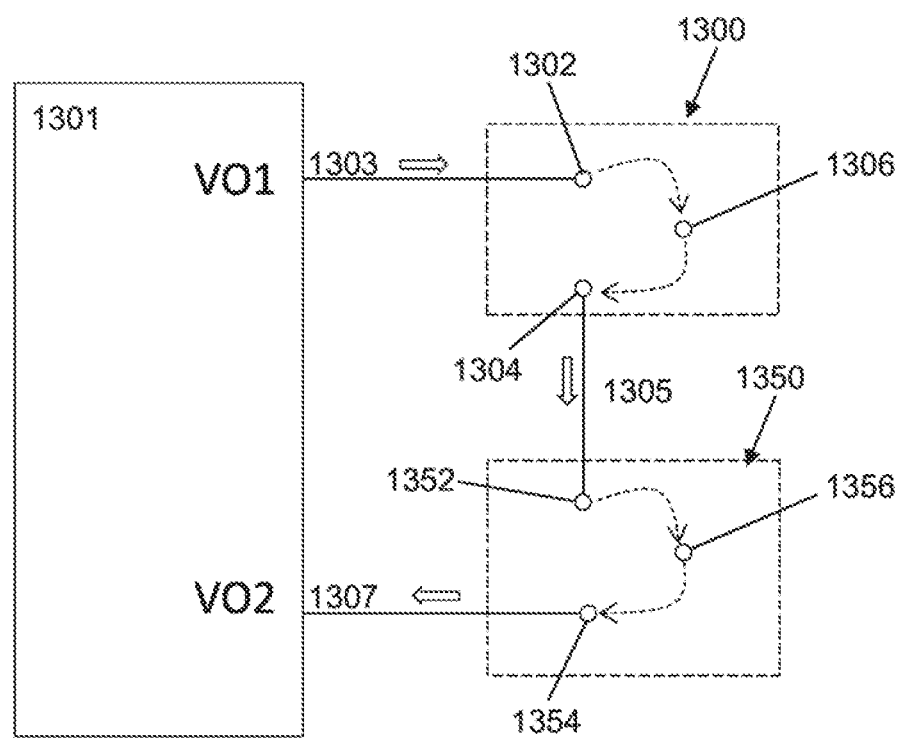
FIG. 13A schematically depicts two shockwave electrode assemblies configured in series.

Alternatively or additionally, two electrode assemblies may be connected in series with respect to each other such that activating a first electrode assembly also activates a second electrode assembly. In some variations, it may be desirable to have multiple shockwave sources without as many wires running along the elongate member, and using fewer ports on the voltage pulse generator. For example, connecting two electrode assemblies in series may allow the shockwave device to simultaneously generate up to four different shockwaves using just two voltage output ports (e.g., one positive channel and one negative channel). In addition, reducing the number of wires that extend along the length of the elongate member would allow the elongate member to bend and flex more freely as it is advanced through the vasculature of a patient (e.g., may allow for a tighter turning radius). One example of a series connection between two electrode assemblies 1300, 1350 is depicted in FIGS. 13A-13D. As schematically depicted in FIG. 13A, a first wire 1303 may connect the first inner electrode 1302 of the first electrode assembly to a first voltage output port VO1 of a pulse generator 1301. A second wire 1305 (e.g., an interconnect wire) may connect the second inner electrode 1304 of the first electrode assembly 1300 to a first inner electrode 1352 of the second electrode assembly 1350. A third wire 1307 may connect the second inner electrode 1354 to a second voltage output port VO2 (a ground channel or negative terminal). In some variations, the first voltage output port VO1 may be a positive channel while the second voltage output port VO2 may be a negative channel (or vice versa). During a high voltage pulse on the first voltage output port VO1, current may flow in the direction of the arrow in the first wire 1303 from the voltage output VO1 to the first inner electrode 1302 of the first electrode assembly 1200. The high voltage pulse generator may apply a voltage pulse on output port VO1 such that the potential difference between the first inner electrode 1302 and the outer electrode 1306 of the first electrode assembly 1300 is high enough to form a plasma arc between them, generating a bubble that gives rise to a shockwave. The current that traverses the bubble from the first inner electrode 1302 to the outer electrode 1306 may set up a potential difference between the outer electrode 1306 and the second inner electrode 1304 that is high enough to form a plasma arc between them, generating a bubble that gives rise to a different shockwave (i.e., a second shockwave). In a variation where the first inner electrode and second inner electrode are located circumferentially opposite to each other (e.g., 180 degrees apart from each other around the circumference of the elongate member), the shockwaves generated by the first and second inner electrodes may propagate in opposite directions, extending outward from the side of the elongate member. The current then flows in the second wire 1305 to the first inner electrode 1352 of the second electrode assembly 1350 and may set up a potential difference between the first inner electrode 1352 and the outer electrode 1356 that is high enough to form a plasma arc between them, generating a bubble that gives rise to another shockwave (i.e., a third shockwave). The current that traverses the bubble from the first inner electrode 1352 to the outer electrode 1356 may set up a potential difference between the outer electrode 1356 and the second inner electrode 1354 of the second electrode assembly 1350 that is high enough to form a plasma arc between them, generating a bubble that gives rise to an additional shockwave (i.e., a fourth shockwave). The current then returns to the voltage source generator via wire 1307 to voltage output port VO2 (which may be a negative channel or a ground channel). Optionally, a connector (not shown) may be provided between the wires 1303, 1307 and the voltage pulse generator 1301 so that the wires of the elongate member may be easily connected to the output ports of the high voltage generator.

Figure 13B:
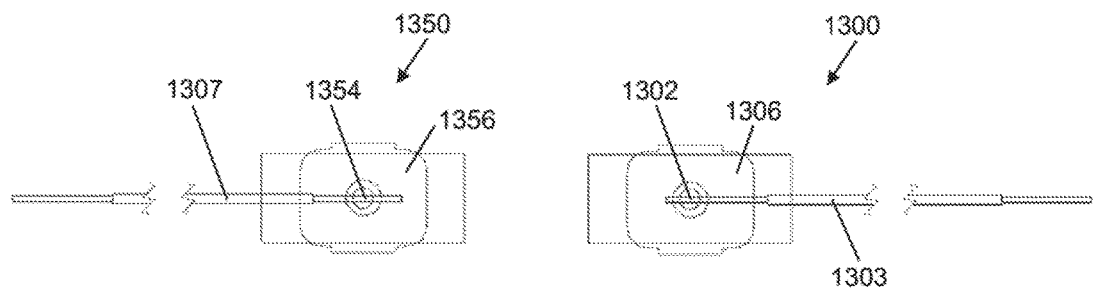
FIGS. 13B-13D depict the connectivity between the inner electrodes and outer electrodes to attain the configuration of FIG. 13A.
Figure 13C:
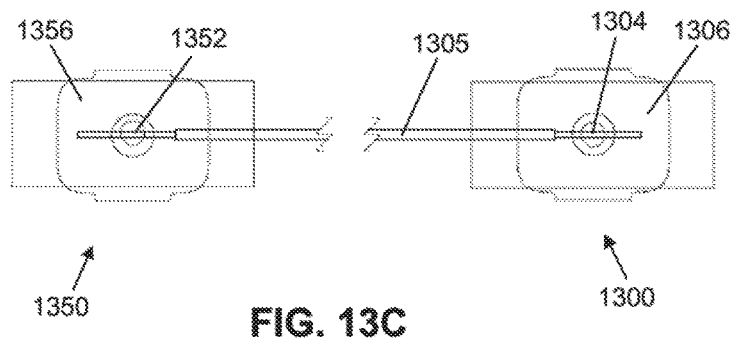
Figure 13D:
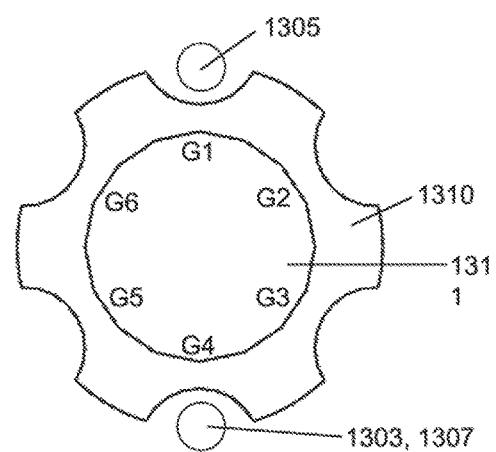

FIGS. 13B-13D depict one variation of how the circuit of FIG. 13A may be implemented in a shockwave device that comprises the first shockwave electrode assembly 1300 and the second shockwave electrode assembly 1350. The shockwave device may comprise a catheter 1310 with a central guide wire lumen 1311 and six longitudinal grooves (G1-G6) arranged around the guide wire lumen. FIG. 13B is a top view of the first and second electrode assemblies 1300, 1350 where the first inner electrode 1302 of the first electrode assembly 1300 and the second inner electrode 1354 of the second electrode assembly 1352 are visible. FIG. 13C a bottom view of the first and second electrode assemblies 1300, 1350 where the second inner electrode 1304 of the first electrode assembly 1300 and the first inner electrode 1356 of the second electrode assembly 1352 are visible. The first and second inner electrodes of each electrode assembly are located circumferentially opposite each other (i.e., 180 degrees apart). FIG. 11D depicts the grooves in which each of the inner electrodes and/or wires may be retained. The wire 1303 connects the first inner electrode 1302 with the first voltage output VO1, and may be retained in a proximal length of groove G4 (i.e., the length of the longitudinal groove that is proximal to the first electrode assembly). The wire 1305 connects the second inner electrode 1304 of the first electrode assembly with the first inner electrode 1352 of the second electrode assembly and may be retained in groove G1, directly opposite groove G4. The wire 1307 connects the second electrode 1354 of the second electrode assembly with the second voltage output VO2, and may be retained in a distal length of groove G4 (i.e., the length of the longitudinal groove that is distal to the second electrode assembly). In some variations, the wire 1307 does not directly connect to the second voltage output port VO2, but instead connects with an additional electrode (e.g., an outer electrode sheath), which is then connected by an additional wire to the second voltage output port. While the example depicted here uses grooves G1, G4, it should be understood that any two of the six grooves may be used to retain the wires 1303, 1305, 1307 to attain the connectivity depicted in FIG. 13A. For example, the wires 1303, 1305, 1307 may be retained in grooves G2 and G5 respectively, or grooves G3 and G6 respectively, etc.

Some variations of shockwave devices comprise a plurality of electrode assemblies, where some of the electrode assemblies are connected in series, while other electrode assemblies are configured such that the first inner electrode and the second inner electrode are each independently voltage-controlled (e.g., each connected to separate ports on a high voltage pulse generator in a direct connect configuration). This may allow for more shockwaves to be simultaneously generated using fewer wires than if all the electrode assemblies were connected to separate voltage channels. Reducing the number of wires along the longitudinal length of the elongate member may help to maintain the ability of the elongate member to bend and flex (e.g., to navigate through tortuous vasculature). This may help the elongate member to have a tighter turning radius, and/or to be able to attain a smaller radius of curvature. An increased number of wires along the length of the elongate member may stiffen the elongate member such that it is no longer able to navigate tortuous vasculature. In some variations, the shockwave force that is generated from electrode assemblies that are connected to a plurality of high voltage channels (e.g., where each inner electrode is connected to a separate voltage channel in a direct connect configuration) may be greater than the shockwave force that is generated from electrode assemblies that are configured in series. In some variations, the voltage applied to electrode assemblies connected in series needs to be greater than the voltage applied to electrode assemblies where each inner electrode is directly connected to a separate voltage channel in order to attain a shockwave of similar magnitude. In some variations, the voltage pulse applied to electrodes in a series configuration may be longer than the voltage pulse applied to electrodes in a direct connect configuration in order to generate shockwaves of similar magnitude. A shockwave device that has a combination of electrode assemblies in both series and direct connect circuit configurations may provide the ability to apply a stronger shockwave when desired, but also have the ability to simultaneously apply many shockwaves without substantially compromising the flexibility and turning capability of the catheter by minimizing the number of wires.

Some shockwave devices may have at least one electrode assembly configured such that its two inner electrodes are connected to separate high voltage channels (i.e., a direct connect configuration) and at least one electrode assembly configured such that its two inner electrodes are connected in series. In still other variations, a shockwave device may have at least one electrode assembly configured such that its two inner electrodes are connected to separate high voltage channels and two or more electrode assemblies that are connected in series. A schematic of a shockwave device that uses both electrode assemblies that are connected in series and in a direct connect configuration is depicted in FIGS. 14A-14G. A shockwave device may have five electrode assemblies located along its length and an elongate member (e.g., a catheter with a longitudinal guide wire lumen) with six grooves extending along its length. The electrode assemblies may be any of the electrode assemblies described herein, and may, for example, each have a first and second inner electrode, an insulating sheath disposed over the inner electrodes, the insulating sheath having first and second openings aligned over the first and second inner electrodes, and an outer electrode sheath disposed over the insulating sheath, the outer electrode sheath having first and second openings aligned over the first and second inner openings of the insulating sheath. The openings of the outer electrode may be larger than the openings of the insulating sheath, and may be coaxially aligned with the openings of the insulating sheath such that the center of the openings are aligned along the same axis. The first and second electrode assemblies 1400, 1420 may be connected in series and controlled together as a pair, and the fourth and fifth electrode assemblies 1440, 1450 may be connected in series and controlled together as a pair, separately from the first and second electrodes. The series connections may be similar to the connection described and depicted in FIGS. 13A-13D. The inner electrodes of the third electrode assembly (which may be located in between the two pairs of series connected electrode assemblies, with the first and second electrode assemblies on one side and the fourth and fifth electrode assemblies on the other side) may be connected in a direct connect configuration, similar to the connected described and depicted in FIGS. 10A-10D. The series connections between the first electrode assembly 1400 and the second electrode assembly 1420 may comprise a first wire 1403 connecting a first voltage output port VO1 to the first inner electrode 1402 of the first electrode assembly 1400, a second wire 1405 (e.g., an interconnect wire) connecting the second inner electrode 1404 of the first electrode assembly to the first inner electrode 1422 of the second electrode assembly 1420, and a third wire 1407 connecting the second inner electrode 1424 of the second electrode assembly to a voltage output port VO5. The third wire 1407 may be part of the current return path to the voltage pulse generator. The series connections between the fourth electrode assembly 1440 and the fifth electrode assembly 1450 may comprise a sixth wire 1413 connecting a fourth voltage output port VO4 to the first inner electrode 1442 of the fourth electrode assembly 1440, a seventh wire 1415 (e.g., an interconnect wire) connecting the second inner electrode 1444 of the fourth electrode assembly to the first inner electrode 1452 of the fifth electrode assembly 1450, and the third wire 1407 connecting the second inner electrode 1454 of the fifth electrode assembly to the voltage output port VO5. The direct connect configuration of the third electrode assembly 1430 may comprise a fourth wire 1409 connecting a second voltage output port VO2 to the first inner electrode 1432 and a fifth wire 1411 connecting a third voltage output port VO3 to the second inner electrode 1434. The outer electrode 1436 may be connected to the voltage output port VO5 via the wire 1407.

Figure 14A:
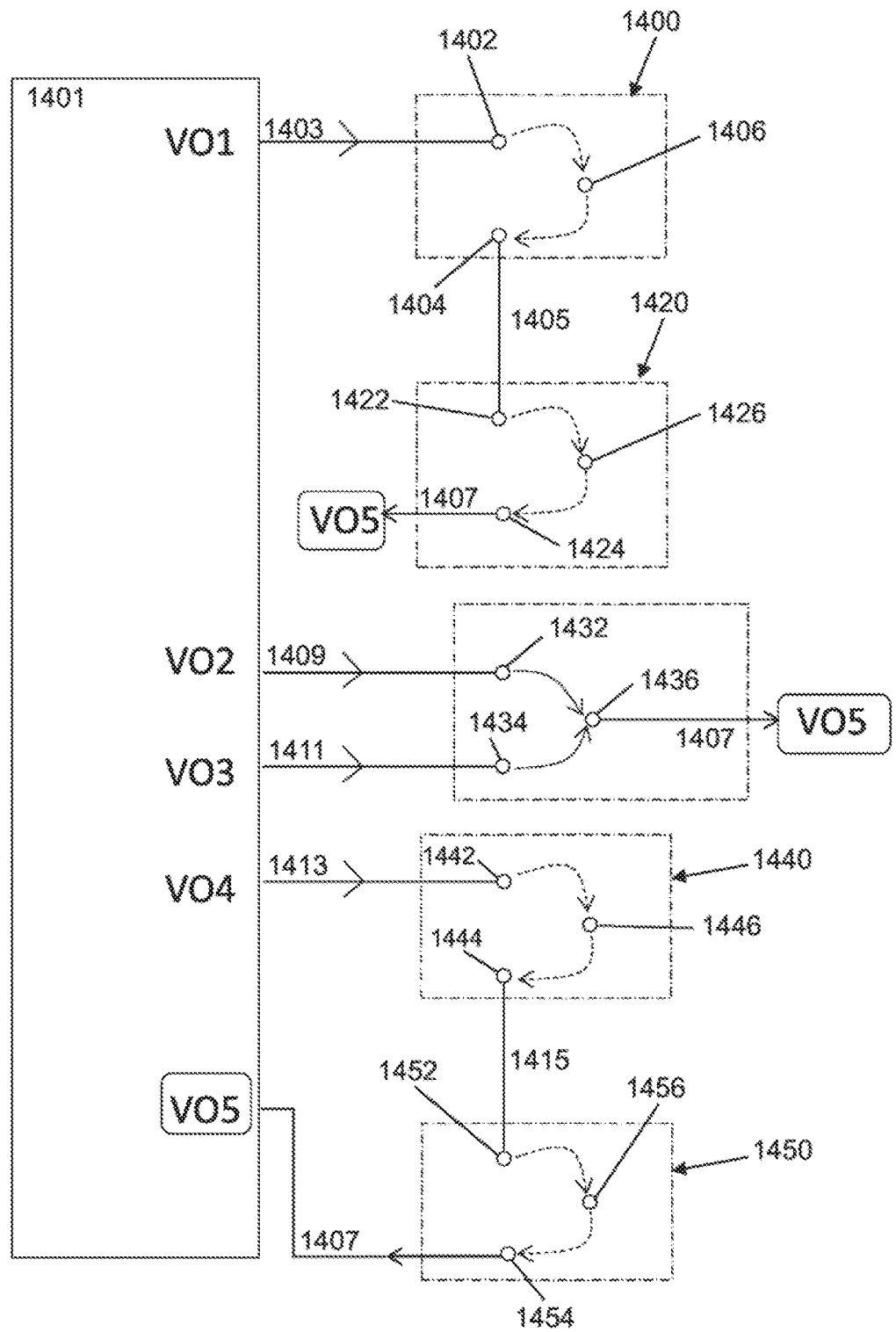
FIG. 14A schematically depicts the connectivity of five shockwave electrode assemblies.
Figure 14B:
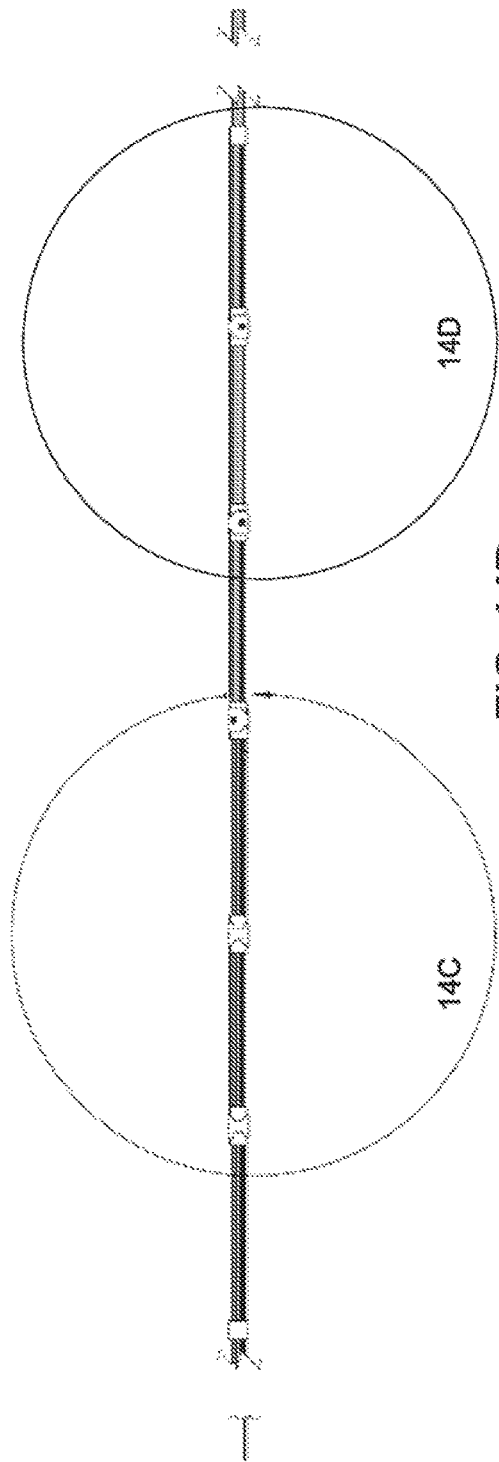
Figure 14C:
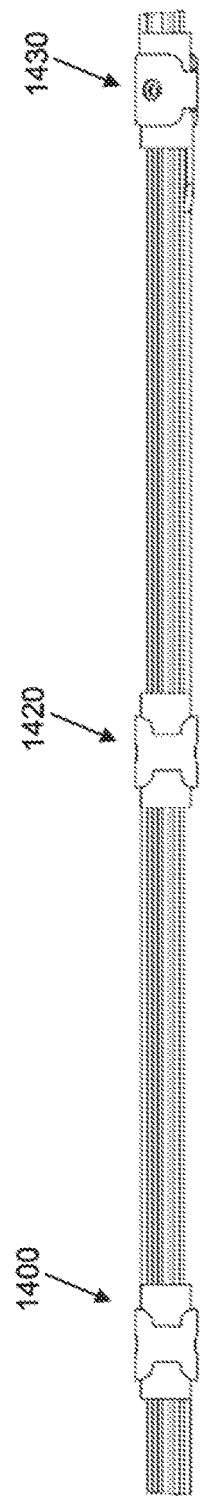

FIGS. 14B-14G depict one variation of how the circuit of FIG. 14A may be implemented in a shockwave device comprising five shockwave electrode assemblies 1400, 1420, 1430, 1440, 1450. The shockwave device may comprise a catheter with a central guide wire lumen and six longitudinal grooves arranged around the guide wire lumen. FIG. 14B is perspective view of the five shockwave assemblies 1400, 1420, 1430, 1440, 1450 along the distal portion of the catheter. The shockwave device depicted there may have a proximal marker band and a distal marker band (e.g., such as angioplasty marker bands). FIG. 14C is a close-up view of the first shockwave electrode assembly 1400, the second shockwave electrode assembly 1420, and the third shockwave assembly 1430. As described above, the first and second electrode assemblies 1400, 1420 may be connected in series, where the wires 1403, 1405, 1407 and inner electrodes 1402, 1404, 1422, 1424 are retained within two of the six grooves, and may for example, be similar to the configuration depicted in FIGS. 13B-13D. Applying a high voltage pulse on wire 1403 may generate four radial shockwaves propagating from circumferentially opposite sides of the catheter. Two of the shockwaves may originate at a longitudinal location along the catheter corresponding to the location of the first electrode assembly 1400 and the other two shockwaves may originate at a longitudinal location along the catheter corresponding to the location of the second electrode assembly 1420. FIG. 14D is a close-up view of the fourth shockwave electrode assembly 1440, the fifth shockwave electrode assembly 1450, and a distal radiopaque marker band 1460. As described above, the fourth and fifth electrode assemblies 1440, 1450 may be connected in series, where the wires 1413, 1415, 1407 and inner electrodes 1442, 1444, 1452, 1454 are retained within two of the six grooves, and may for example, be similar to the configuration depicted in FIGS. 13B-13D. In some variations, the wires and inner electrodes may be in a pair of grooves that are different from the pair of grooves retaining the wires and inner electrodes of the first and second electrode assemblies. Applying a high voltage pulse on wire 1413 may generate four radial shockwaves propagating from circumferentially opposite sides of the catheter. Two of the shockwaves may originate at a longitudinal location along the catheter corresponding to the location of the fourth electrode assembly 1440 and the other two shockwaves may originate at a longitudinal location along the catheter corresponding to the location of the fifth electrode assembly 1450.

FIG. 14E is a close-up view of the fifth electrode assembly 1450 and the distal marker band 1460. In some variations of shockwave devices, the wire connected to the second inner electrode 1454 of the fifth electrode assembly 1450 may be connected to the distal marker band 1460. The distal marker band 1460 may act as a common node for wires that carry the return currents from the electrode assemblies, which may help reduce the number of wires carrying a return current back to the high voltage pulse generator. There may be several of such return path nodes along the length of the catheter, and may be, for example, one or more additional radiopaque marker bands, and/or one or more outer electrode sheaths of certain electrode assemblies.

Figure 14F:
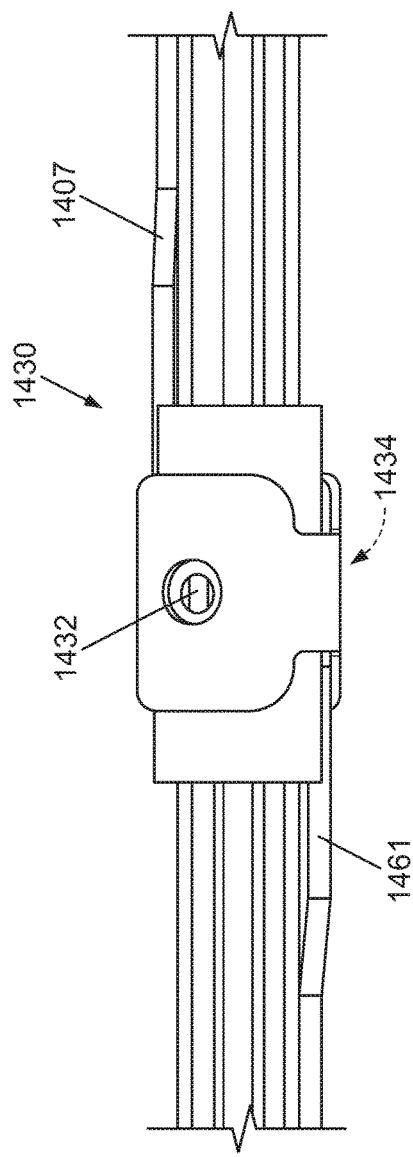
Figure 14G:
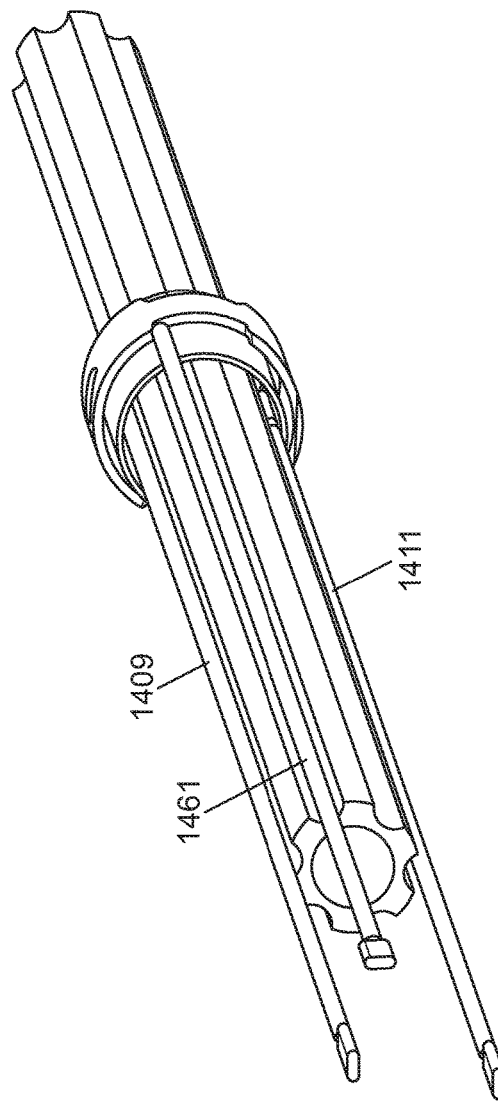

FIG. 14F is a close-up view of the third electrode assembly 1430. As described above, the inner electrode 1432 and inner electrode 1434 (which is not visible in this view) may be in a direct connect configuration such that they may be individually driven by separate outputs from the voltage generator. The currents from the inner electrodes may flow to the outer electrode 1436, which may return the current to the high voltage pulse generator via the third wire 1407. Alternatively, or additionally, the current from the outer electrode 1436 may return to the high voltage pulse generator via an eighth wire 1461. The eighth wire 1461 may be retained in a groove that is opposite the groove that retains the third wire 1407. FIG. 14G depicts the wires 1409, 1411, 1461 retained within three grooves of the catheter, where the wires 1409, 1411 are connected to the inner electrodes 1432, 1434, and retained in grooves that are opposite to each other. The wire 1461 may contact the outer electrode 1436 and may be retained in a third groove (similar to the configuration described and depicted in FIGS. 10A-10D).

While FIGS. 14A-14F depict a shockwave device with five electrode assemblies located along the length of the elongate member, it should be understood that a shockwave device may have any number of electrode assemblies connected in any combination of series and direct connect configurations. For example, a shockwave device may have two electrode assemblies that are connected to each other in series, which may allow for the synchronized generation of four different shockwaves simultaneously. Alternatively, a shockwave device may have two electrode assemblies where the two inner electrodes of each assembly are each connected to separate high voltage channels in a direct connect configuration, which may allow for the independent generation of four different shockwaves, either simultaneously or sequentially. The number of electrode assemblies along the length of the elongate member of a shockwave device may be selected according to the geometry of the target tissue region. For example, a shockwave device intended for breaking up calcified plaques along a long vessel segment may have five electrode assemblies along its length, while a device for breaking up plaques in a shorter vessel segment may have two electrode assemblies along its length.

Any of the shockwave assemblies described herein may be used in an angioplasty procedure for breaking up calcified plaques accumulated along the walls of a vessel. One variation of a method may comprise advancing a guide wire from an entry site on a patient (e.g., an artery in the groin area of the leg) to the target region of a vessel (e.g., a region having calcified plaques that need to be broken up). A shockwave device comprising a catheter with a guide wire lumen, one or more low-profile electrode assemblies located along a length of the catheter, and a balloon may be advanced over the guide wire to the target region of the vessel. The shockwave electrode assemblies may be any of the low-profile electrode assemblies described herein. The balloon may be collapsed over the catheter while the device is advanced through the vasculature. The location of the shockwave device may be determined by x-ray imaging and/or fluoroscopy. When the shockwave device reaches the target region, the balloon may be inflated by a fluid (e.g., saline and/or saline mixed with an image contrast agent). The one or more electrode assemblies may then be activated to generate shockwaves to break up the calcified plaques. The progress of the plaque break-up may be monitored by x-ray and/or fluoroscopy. The shockwave device may be moved along the length of the vessel if the calcified region is longer than the length of the catheter with the electrode assemblies, and/or if the calcified region is too far away from the electrode assemblies to receive the full force of the generated shockwaves. For example, the shockwave device may be stepped along the length of a calcified vessel region to sequentially break up the plaque. The electrode assemblies of the shockwave device may be connected in series and/or may be connected such that each inner electrode is connected to separate high voltage channels, and may be activated simultaneously and/or sequentially, as described above. For example, a pair of electrode assemblies may be connected in series and activated simultaneously, while another electrode assembly may be connected such that each inner electrode is connected to separate high voltage channels, and activated sequentially and/or simultaneously. Once the calcified region has been sufficiently treated, the balloon may be inflated further or deflated, and the shockwave device and guide wire may be withdrawn from the patient.

It will be understood that the foregoing is only illustrative of the principles of the invention, and that various modifications, alterations and combinations can be made by those skilled in the art without departing from the scope and spirit of the invention. Any of the variations of the various shockwave devices disclosed herein can include features described by any other shockwave devices or combination of shockwave devices herein. Furthermore, any of the methods can be used with any of the shockwave devices disclosed. Accordingly, it is not intended that the invention be limited, except as by the appended claims. For all of the variations described above, the steps of the methods need not be performed sequentially.

What is claimed as new and desired to be protected by Letters Patent of the United States is:

1. A method for cracking calcified lesions at a target region in a blood vessel of a patient comprising the steps of:
    advancing a guide wire from an entry site on a patient to the target region of the vessel;
    advancing a catheter over the guide wire, said catheter including an electrode assembly surrounded by a semi-rigid enclosure and wherein a first wire extends along the length of the catheter, said first wire being insulated and having a non-insulated portion defining a first inner electrode and wherein a second wire extends along a length of the catheter, said second wire being insulated and having a non-insulated portion defining a second inner electrode, said second inner electrode being located at a position circumferentially offset from the first inner electrode, said electrode assembly further including a conductive sheath having first and second apertures arcuate cut-outs formed therein, said conductive sheath being mounted on the catheter so that the first arcuate cut-out thereof is aligned with the first inner electrode and the second arcuate cut-out thereof is aligned with the second inner electrode;

filling the enclosure with a conductive fluid; and supplying at least one high voltage pulse to the first and second wires so that shockwaves will be generated near both the first and second inner electrodes, with a series connection being defined as the current travels along a path extending from the first inner electrode to the conductive sheath and from the conductive sheath to the second inner electrode, with the shock waves cracking the calcified lesion.

2. A method as recited in claim 1 wherein after the one or more high voltage pulses are supplied to the first and second wires, the catheter is repositioned within the vessel and additional high voltage pulses are supplied to the first and second wires.

3. A method as recited in claim 1 wherein the first and second inner electrodes are further defined by an additional conductive element attached to each of the non-insulated portions of the first and second wires.

4. A method as recited in claim 3 wherein the additional conductive element is a hypotube crimped to each of the non-insulated portions of the first and second wires.

5. A method as recited in claim 1 wherein the first and second wires each include an insulated sheath.

6. A method as recited in claim 5 wherein the catheter includes elongated grooves formed along the outer surface thereof and wherein the first and second wires are carried in the grooves.

7. A method as recited in claim 1 wherein the second inner electrode is offset from the first inner electrode by 180 degrees.

8. A method as recited in claim 1 further including a second conductive sheath having first and second arcuate cut-outs therein and wherein the second inner electrode is connected to a third inner electrode, said third inner electrode being aligned with the first arcuate cut-out in the second conductive sheath and a fourth inner electrode is aligned with the second arcuate cut-out in the second conductive sheath.

9. A method as recited in claim 1 further including an insulating sheath mounted between the conductive sheath and the first and second inner electrodes, the insulating sheath including first and second arcuate cut-outs respectively aligned with the first and second arcuate cut-outs of the conductive sheath.

10. A method as recited in claim 1 wherein the enclosure is an inflatable balloon.

11. A method for cracking calcified lesions at a target region in a blood vessel of a patient comprising the steps of:

advancing a guide wire from an entry site on a patient to the target region of the vessel;

advancing a catheter over the guide wire, said catheter including an electrode assembly surrounded by a semi-rigid enclosure and wherein a first wire extends along the length of the catheter, said first wire being insulated and having a non-insulated portion defining a first inner electrode and wherein a second wire extends along a length of the catheter, said second wire being insulated and having a non-insulated portion defining a second inner electrode, said second inner electrode being located at a position circumferentially offset from the first inner electrode, said second wire having a second non-insulated portion defining a third inner electrode axially spaced from the first inner electrode along the length of the catheter, said electrode assembly further including a first conductive sheath having first and second arcuate cut-outs formed therein, said first conductive sheath being mounted on the catheter so that the first arcuate cut-out is aligned with the first inner electrode and the second arcuate cut-out thereof is aligned with the second inner electrode, a third wire extending along a length of the catheter, said wire being insulated and having a non-insulating portion defining a fourth inner electrode, said fourth inner electrode being located at a position circumferentially offset from the third inner electrode and substantially at the same axial location as the third inner electrode, said electrode assembly including a second conductive sheath having first and second arcuate cut-outs formed therein, said second conductive sheath being mounted on the catheter so that the first arcuate cut-out thereof is aligned with the third inner electrode and the second arcuate cut-out thereof is aligned with the fourth inner electrode;

filling the enclosure with a conductive fluid; and supplying at least one high voltage pulse to the first and third wires so that shockwaves will be generated near each of the first, second, third and fourth inner electrodes, with a series connection being defined as the current travels along a path extending from the first inner electrode to the first conductive sheath and from the first conductive sheath to the second inner electrode and from the second inner electrode to the third inner electrode, and from the third inner electrode to the second conductive sheath and from the second conductive sheath to the fourth inner electrode with the shock waves cracking the calcified lesion.

12. A method as recited in claim 11 wherein after the one or more high voltage pulses are supplied to the first and third wires, the catheter is repositioned within the vessel and additional high voltage pulses are supplied to the first and third wires.

13. A method as recited in claim 11 wherein the first, second and third wires each include an insulated sheath.

14. A method as recited in claim 13 wherein the catheter includes elongated grooves formed along the outer surface thereof and wherein the first, second and third wires are carried in the grooves.

15. A method as recited in claim 11 wherein the second inner electrode is offset from the first inner electrode by 180 degrees and the fourth inner electrodes is offset form the third inner electrode by 180 degrees.

16. A method as recited in claim 11 further including a first insulating sheath mounted between the first conductive sheath and the first and second inner electrodes, the first insulating sheath including first and second arcuate cut-outs respectively aligned with the first and second arcuate cut-outs of the conductive sheath, said device further including a second insulating sheath mounted between the second conductive sheath and the third and fourth inner electrodes, the second insulating sheath including first and second arcuate cut-outs respectively aligned with the first and second arcuate cut-outs of the second conductive sheath.

17. A method as recited in claim 11 wherein the enclosure is an inflatable balloon.

* * * * *